(12) United States Patent
Oh et al.

(10) Patent No.: US 8,779,183 B2
(45) Date of Patent: Jul. 15, 2014

(54) ACID GENERATING AGENT FOR CHEMICALLY AMPLIFIED RESIST COMPOSITIONS

(75) Inventors: Jung-Hoon Oh, Chungcheongnam-do (KR); Dong-Cheol Seo, Chungcheongnam-do (KR); Hyun-Sang Joo, Chungcheongnam-do (KR); Chang-Soo Lee, Seoul (KR)

(73) Assignee: Korea Kumho Petrochemical Co., Ltd., Chongno-Gu, Seoul (KR)

( * ) Notice: Subject to any disclaimer, the term of this patent is extended or adjusted under 35 U.S.C. 154(b) by 1722 days.

(21) Appl. No.: 12/214,429

(22) Filed: Jun. 19, 2008

(65) Prior Publication Data

US 2009/0234155 A1 Sep. 17, 2009

(30) Foreign Application Priority Data

Mar. 13, 2008 (KR) ........................ 10-2008-0023406

(51) Int. Cl.
*C07C 309/17* (2006.01)

(52) U.S. Cl.
USPC .............................. 562/100; 562/41; 562/109

(58) Field of Classification Search
USPC ............... 562/1, 117, 119, 120, 122, 126, 41, 562/100, 109
See application file for complete search history.

(56) References Cited

U.S. PATENT DOCUMENTS

| 7,611,822 B2* | 11/2009 | Takemoto ................... 430/270.1 |
| 8,026,390 B2* | 9/2011 | Oh et al. ......................... 562/41 |
| 8,246,110 B2* | 8/2012 | Katayama et al. ............. 296/217 |

* cited by examiner

*Primary Examiner* — Sudhakar Katakam
*Assistant Examiner* — Pancham Bakshi
(74) *Attorney, Agent, or Firm* — Davidson, Davidson & Kappel, LLC

(57) ABSTRACT

An acid generating agent used for chemically amplified resist compositions is provided, which agent is represented by the following formula (1):

[Formula 1]

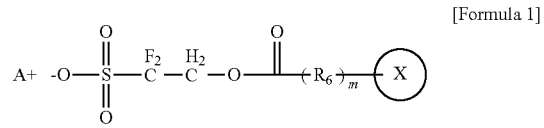

wherein X represents a monocyclic or polycyclic hydrocarbon group having 3 to 30 carbon atoms, and having at least one hydrogen atom on the ring substituted by an alkyl or alkoxy group which may be unsubstituted or substituted with a group selected from an ether group, an ester group, a carbonyl group, an acetal group, an epoxy group, a nitrile group and an aldehyde group, or by a perfluoroalkyl group, a hydroxyalkyl group, or a cyano group; $R_6$ is an alkyl group, an alkoxy group, or a heteroatom selected from the group consisting of N, S and F; m is an integer from 0 to 2; and A+ is an organic counterion.

13 Claims, 11 Drawing Sheets

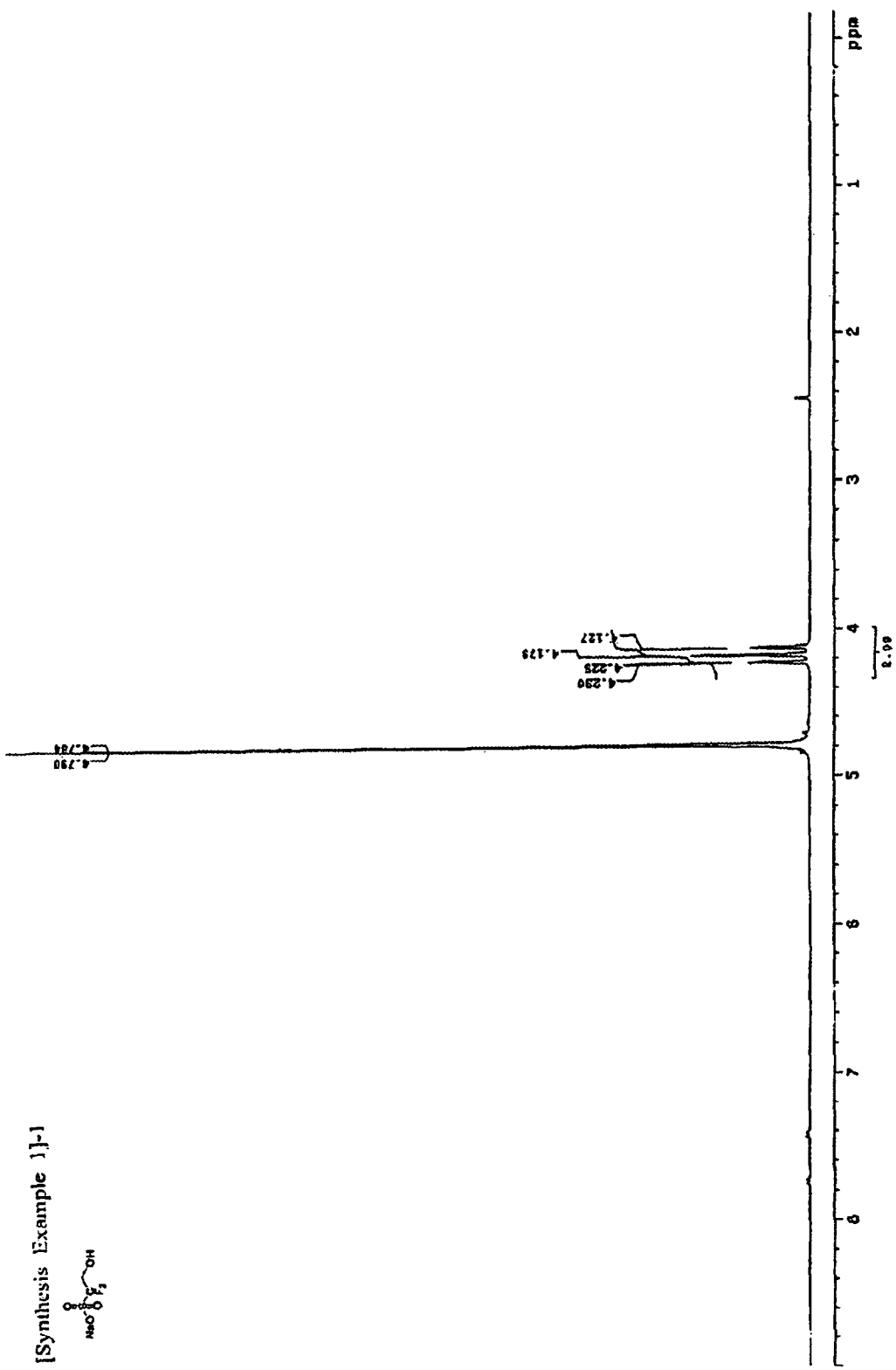
FIG. 1
[Synthesis Example 1]-1
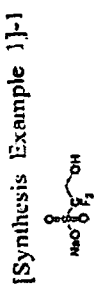

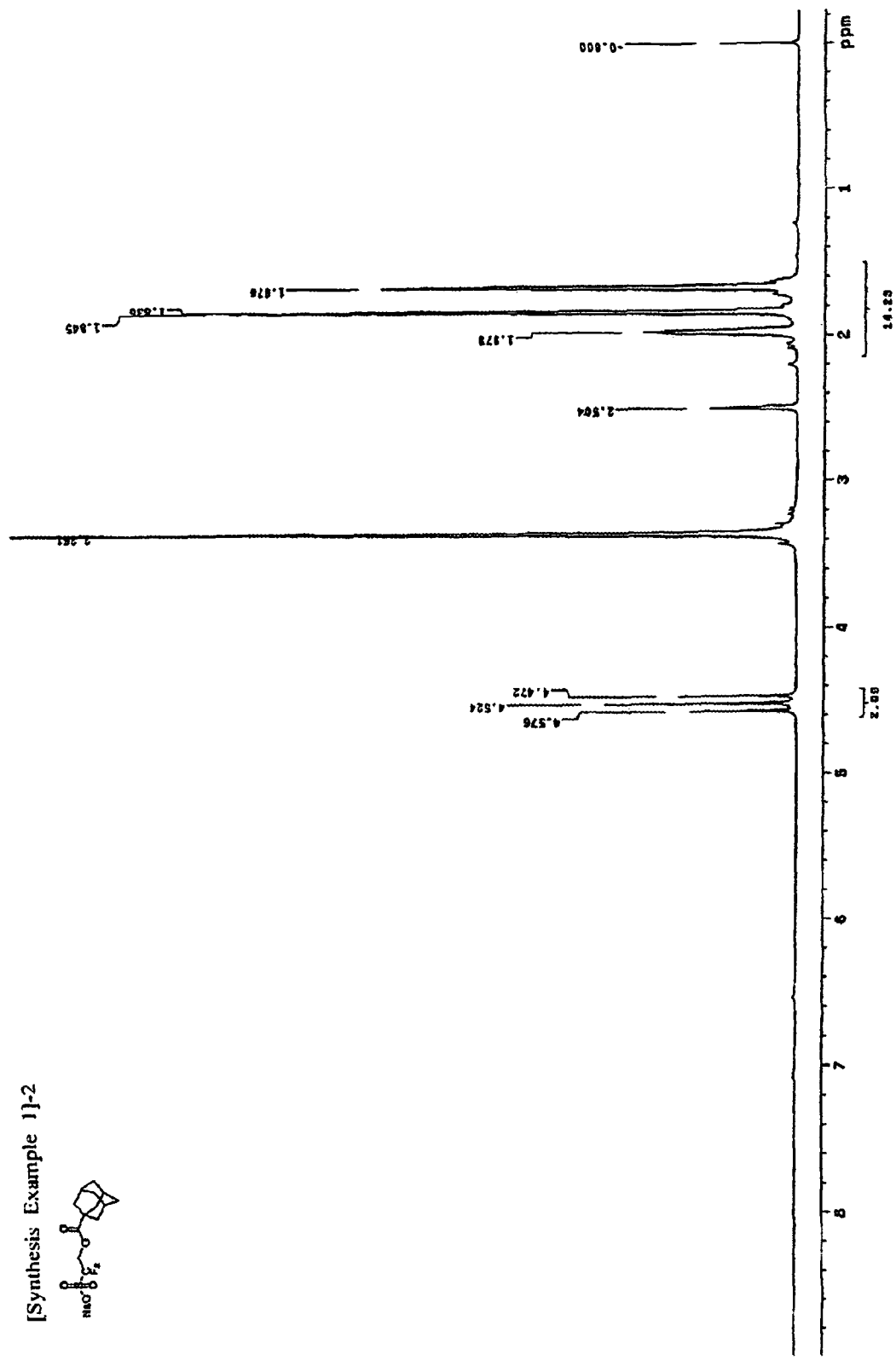
FIG.2
[Synthesis Example 1]-2
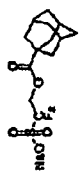

[Synthesis Example 2]-1

ACID GENERATING AGENT FOR CHEMICALLY AMPLIFIED RESIST COMPOSITIONS

CROSS-REFERENCE TO RELATED APPLICATION

This application claims priority under 35 U.S.C & 119 from Korean Patent Application 10-2008-0023406, filed on Mar. 13, 2008, the contents of which are hereby incorporated by reference in their entirety for all purposes as if fully set forth herein.

BACKGROUND OF THE INVENTION

1. Field of the Invention The present invention relates to an acid generating agent, and more particularly, to a salt useful as an acid generating agent contained in chemically amplified resist compositions that are used in semiconductor processes.

2. Description of the Related Art

A chemically amplified resist composition used in the semiconductor fine processing utilizing lithography contains an acid generating agent, and as the technologies supporting the semiconductor fine processing continue to develop, a demand for resists with higher resolution still exists.

Therefore, in order to produce a resist having an increased resolution and desired properties, a large number of different acid generating agents have been developed, and in particular, numerous modifications and experiments in design have been carried out concerning the cation part of salts that are used as photo-acid generating agents, so as to improve the diffusion rate of acid and transparency, which are important properties required from an acid generating agent.

However, in the recent research on resist compositions, the improvement of the properties of resist based on the cation of photo-acid generating agents is facing the limit, and there is rising another problem of reducing the amount of the salt of a photo-acid generating agent eluted into water, as water is used in the processes of argon fluoride (ArF) immersion lithography.

Therefore, in recent years, the development of acid generating agents is being achieved with more focus on the anion part, on the bases of numerous experimental results and reports showing that the anion moiety has substantially greater influence than the cation moiety in terms of the physical and chemical characteristics which can improve the fluidity of acid and the properties of the resist composition. Now, the trend of the development is inclined toward photo-acid generating agents which are capable of reducing the diffusion rate of acid, and have good transmissibility of ArF laser at 193 nm. Accordingly, there are competitive attempts to introduce a bulky alicyclic ring into the anion of a salt which is suitable as a photo-acid generating agent.

SUMMARY OF THE INVENTION

In an attempt to address such problems as described above, there is provided, according to an aspect of the present invention, a novel acid generating agent useful for chemically amplified resist compositions, which agent has excellent resolution and line width roughness, and is eluted less readily into water in the processes of ArF immersion lithography.

According to another aspect of the present invention, there is provided an intermediate used in the production of the acid generating agent, and a method for synthesizing the intermediate substance.

The acid generating agent according to embodiments of the present invention is represented by the following formula (1).

[Formula 1]

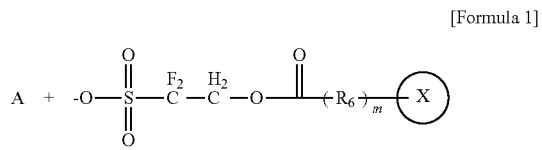

wherein X represents a monocyclic or polycyclic hydrocarbon group having 3 to 30 carbon atoms, and having at least one hydrogen atom on the ring substituted by an alkyl or alkoxy group which has 1 to 10 carbon atoms and may be unsubstituted or substituted with a group selected from an ether group, an ester group, a carbonyl group, an acetal group, an epoxy group, a nitrile group and an aldehyde group, or by a perfluoroalkyl group having 1 to 4 carbon atoms, a hydroxyalkyl group having 1 to 10 carbon atoms, or a cyano group; $R_6$ is an alkyl group having 1 to 10 carbon atoms, an alkoxy group having 1 to 10 carbon atoms, or a heteroatom selected from the group consisting of nitrogen (N), sulfur (S) and fluorine (F); m is an integer from 0 to 2; and A+ is an organic counterion.

Specific examples of the ring X include a monocyclic hydrocarbon group having 3 to 12 carbon atoms, a bicyclic hydrocarbon group having 8 to 20 carbon atoms, a tricyclic hydrocarbon group having 10 to 30 carbon atoms, a tetracyclic hydrocarbon group having 10 to 30 carbon atoms, and the like.

Also, the X represents an adamantyl group, a norbornyl group or a cycloalkyl group.

Such monocyclic, bicyclic, tricyclic and tetracyclic groups may be exemplified by the compounds represented by the following formulas (1-a) to (1-h).

[Formulas 1-a to 1-h]

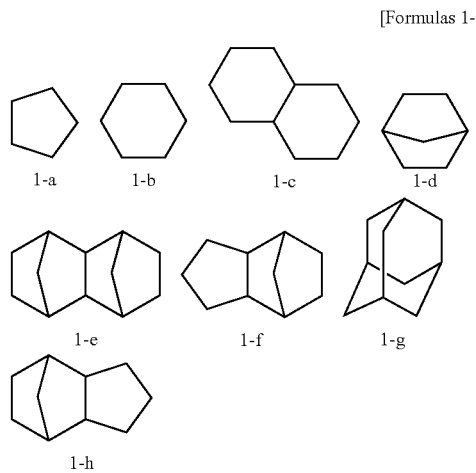

The ring X has one hydrogen atom at any position bound to an adjacent group, and at least one hydrogen atom among the hydrogen atoms present on the ring excluding the hydrogen atom bound to an adjacent group, is substituted by an alkyl or alkoxy group having 1 to 10 carbon atoms, a hydroxyalkyl group having 1 to 10 carbon atoms, or the like.

The anion represented by the formula (1) according to an embodiment of the present invention may be exemplified by compounds represented by the following formulas (1-i) to (1-xx):

[Formulas 1-i to 1-xx]
1-i
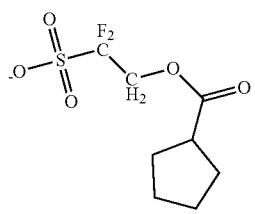
1-ii
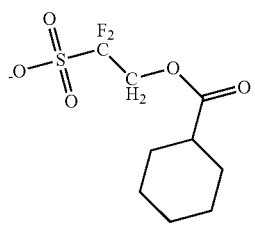
1-iii
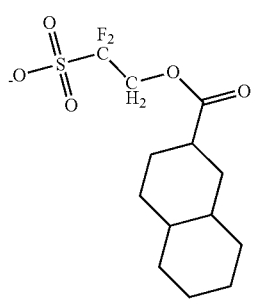
1-iv
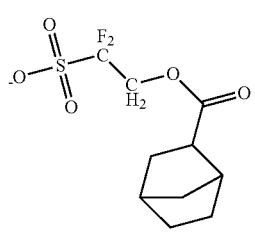
1-v
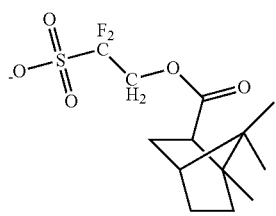
1-vi
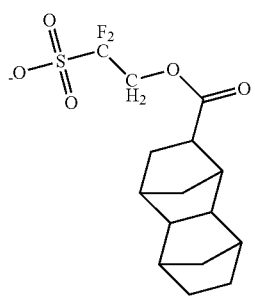
1-vii
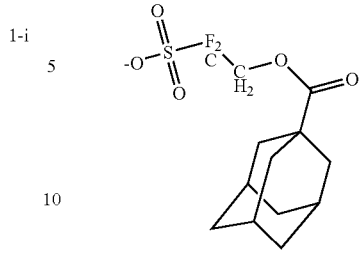
1-viii
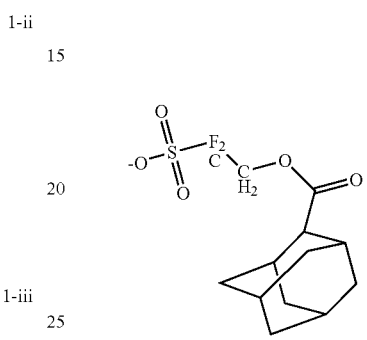
1-ix
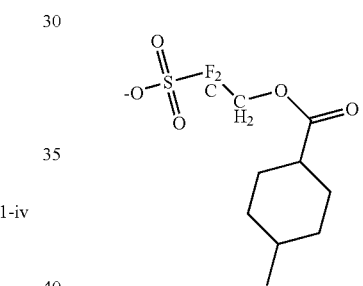
1-x
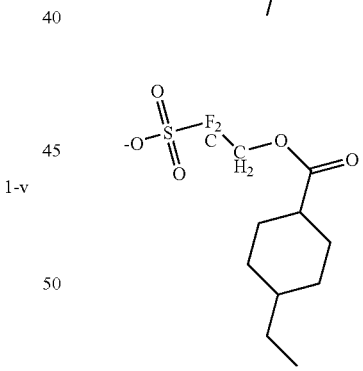
1-xi
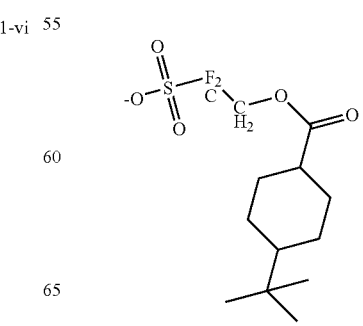

1-xii
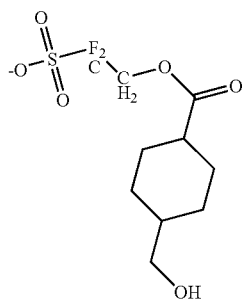
1-xiii
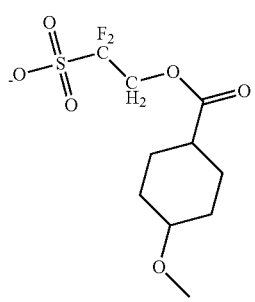
1-xiv
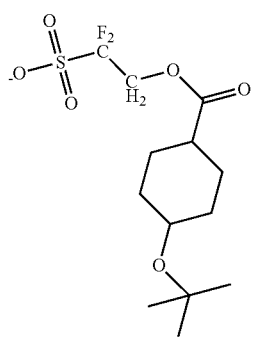
1-xv
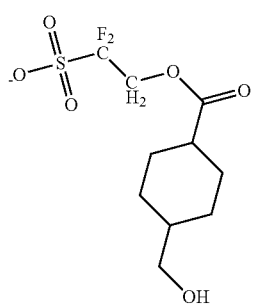
1-xvi
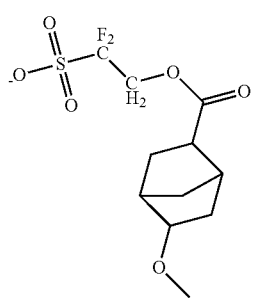
1-xvii
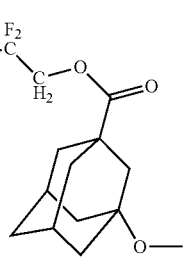
1-xviii
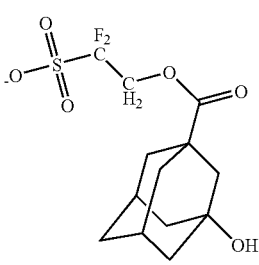
1-xix
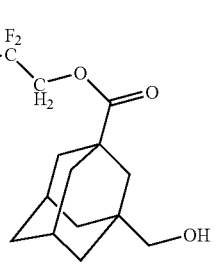
1-xx
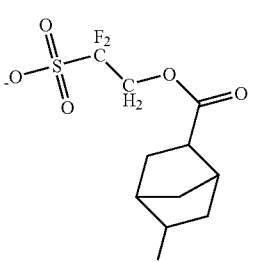
In the formula (1), A+ represents an organic counterion, and examples thereof include ions represented by the following formulas (2a), (2b), (3a) and (3b), and the like:
[Formula 2a]
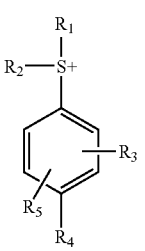

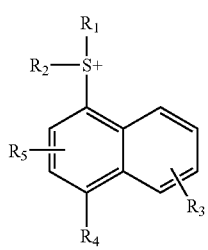

[Formula 2b]

wherein in the formulas (2a) and (2b), $R_1$ and $R_2$ each independently represent an alkyl group, an allyl group, a perfluoroalkyl group, a benzyl group or an aryl group; and $R_3$, $R_4$ and $R_5$ each independently represent a hydrogen atom, an alkyl group, a halogen group, an alkoxy group, an aryl group, a thiophenoxy group, a thioalkoxy group or an alkoxycarbonylmethoxy group.

More specific examples of these substituents include, as the alkyl group, a methyl group, an ethyl group, a propyl group, an isopropyl group, an n-butyl group, a phenyl group, a hexyl group, an octyl group and the like; and as the alkoxy group, a methoxy group, an ethoxy group, a propoxy group, a butoxy group, a hexyloxy group, an octyloxy group and the like.

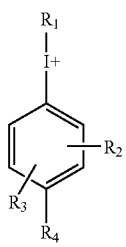

[Formula 3a]

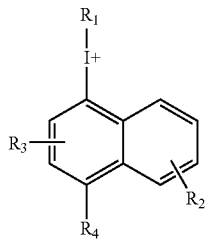

[Formula 3b]

wherein in the formulas (3a) and (3b), $R_1$ and $R_4$ each independently represent an alkyl group, an allyl group, a perfluoroalkyl group, a benzyl group or an aryl group; and $R_2$ and $R_3$ each independently represent a hydrogen atom, an alkyl group, a halogen group, an alkoxy group, an aryl group, a thiophenoxy group, a thioalkoxy group or an alkoxycarbonylmethoxy group.

More specific examples of these substituents include, as the alkyl group, a methyl group, an ethyl group, a propyl group, an isopropyl group, an n-butyl group, a phenyl group, a hexyl group, an octyl group and the like; and as the alkoxy group, a methoxy group, an ethoxy group, a propoxy group, a butoxy group, a hexyloxy group, an octyloxy group and the like.

Furthermore, specific examples of the ions of formula 2a or 2b include those selected from the group consisting of ions represented by the following formulas (2-i) to (2-xx):

[Formulas 2-i to 2-xx]

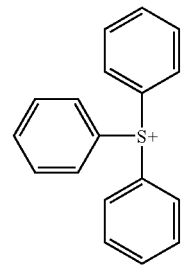

2-i

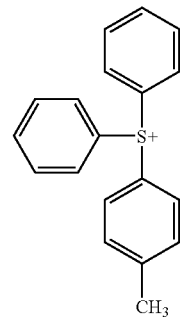

2-ii

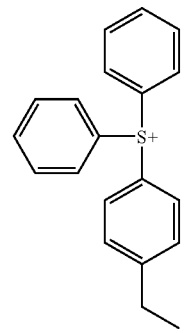

2-iii

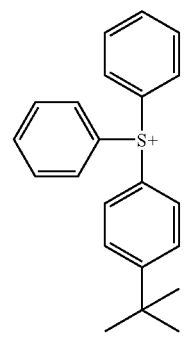

2-iv

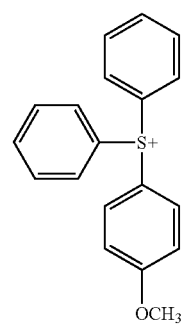

2-v

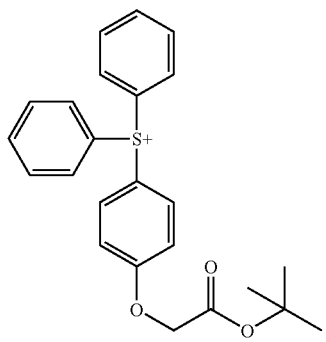
2-vi
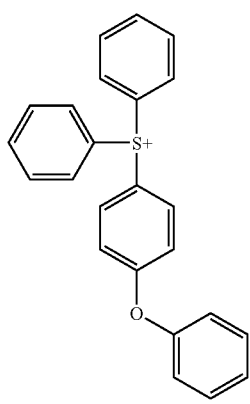
2-vii
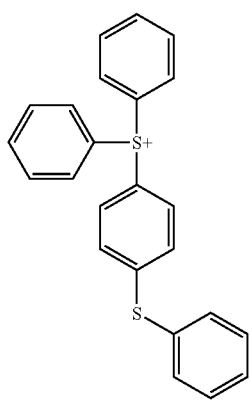
2-viii
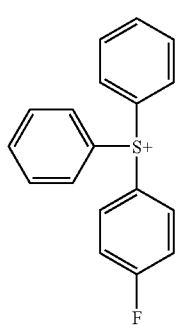
2-ix
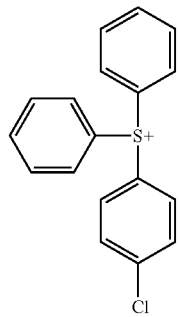
2-x
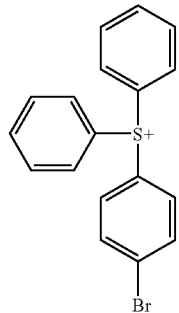
2-xi
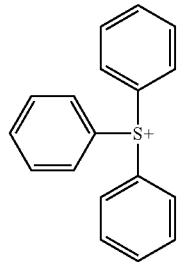
2-xii
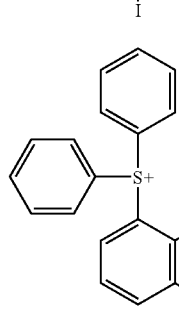
2-xiii
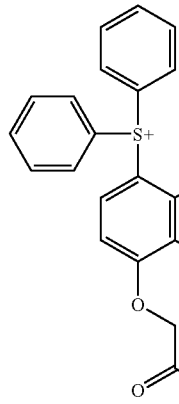
2-xiv

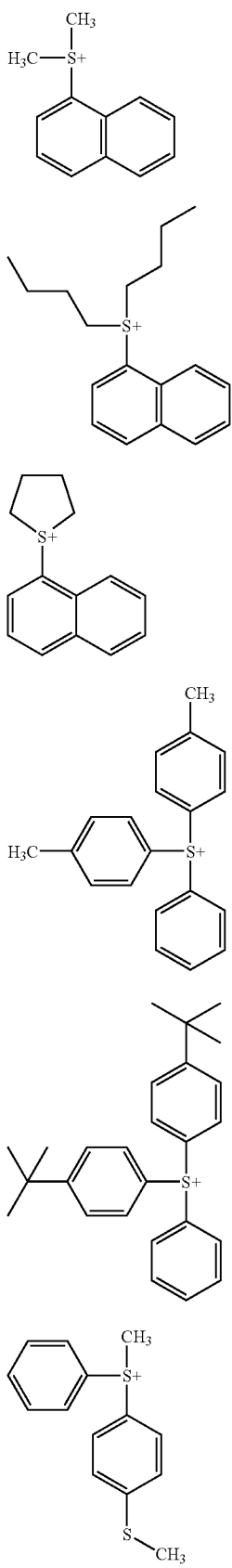
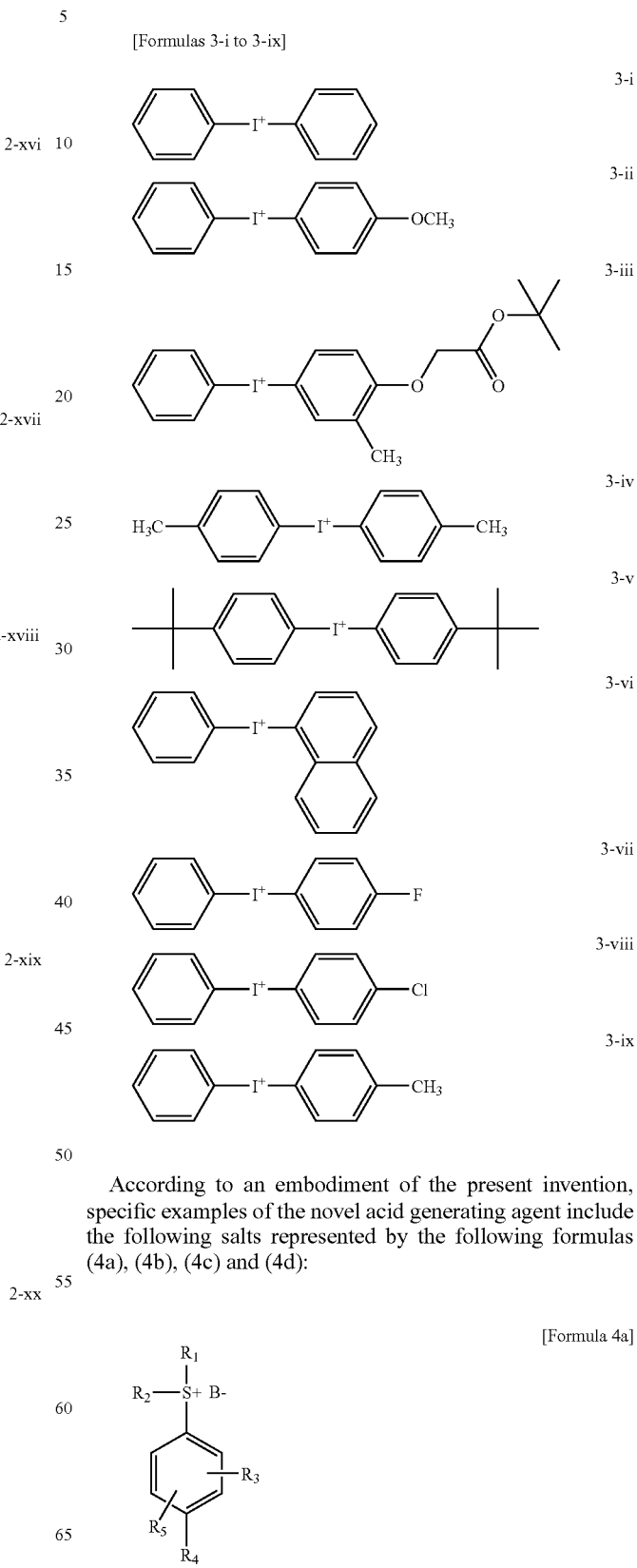
Specific examples of the ions of formula (3a) or (3b) include those selected from the group consisting of ions represented by the following formulas (3-i) to (3-ix):
According to an embodiment of the present invention, specific examples of the novel acid generating agent include the following salts represented by the following formulas (4a), (4b), (4c) and (4d):

[Formula 4b]

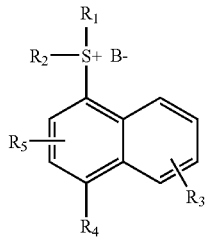

[Formula 4c]

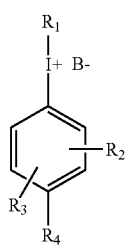

[Formula 4d]

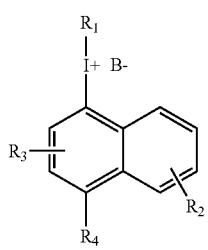

In the formulas (4a) and (4b), $R_1$ and $R_2$ each independently represent an alkyl group, an allyl group, a perfluoroalkyl group, a benzyl group or an aryl group; and $R_3$, $R_4$ and $R_5$ each independently represent a hydrogen atom, an alkyl group, a halogen atom, an alkoxy group, an aryl group, a thiophenoxy group, a thioalkoxy group or an alkoxycarbonylmethoxy group. In the formulas (4c) and (4d), $R_1$ represents an alkyl group, an allyl group, a perfluoroalkyl group, a benzyl group or an aryl group; and $R_2$, $R_3$ and $R_4$ each independently represent a hydrogen atom, an alkyl group, a halogen atom, an alkoxy group, an aryl group, a thiophenoxy group, a thioalkoxy group or an alkoxycarbonylmethoxy group. In all of the above formulas, B commonly represents the following formula (5), (6) or (7):

[Formula 5]

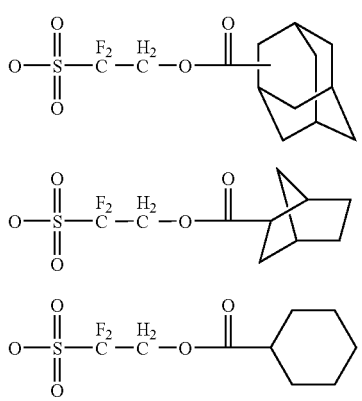

[Formula 6]

[Formula 7]

Hereinafter, the method for producing an acid generating agent represented by the formula (1) will be discussed.

According to an embodiment of the present invention, as the method for producing a salt represented by the formula (1), there may be used a method including reacting a compound represented by the following Formula (8) with a compound represented by the following formula (12) at a temperature of 0 to 100° C., using a mixture of water and an organic solvent such as dichloromethane, chloroform or dichloroethane:

[Formula 8]

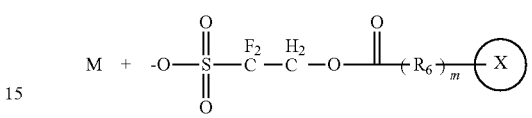

$A^+Z^-$ [Formula 12]

wherein in the above formulas (8) and (12), X represents a monocyclic or polycyclic hydrocarbon group having 3 to 30 carbon atoms, and having at least one hydrogen atom on the ring substituted by an alkyl or alkoxy group which has 1 to 10 carbon atoms and may be unsubstituted or substituted with a group selected from an ether group, an ester group, a carbonyl group, an acetal group, an epoxy group, a nitrile group and an aldehyde group, or by a perfluoroalkyl group having 1 to 4 carbon atoms, a hydroxyalkyl group having 1 to 10 carbon atoms, or a cyano group; $R_6$ is an alkyl group having 1 to 10 carbon atoms, an alkoxy group having 1 to 10 carbon atoms, or a heteroatom selected from the group consisting of N, S and F; m is an integer from 0 to 2; M is lithium (Li), sodium (Na) or potassium (K); Z is $OSO_2CF_3$, $OSO_2C_4F_9$, $OSO_2C_8F_{17}$, $N(CF_3)_2$, $N(C_2F_5)_2$, $N(C_4F_9)_2$, $C(CF_3)_3$, $C(C_2F_5)_3$, $C(C_4F_9)_3$, fluorine (F), chlorine (Cl), bromine (Br), iodine (I), $BF_4$, $ASF_6$ or $PF_6$; and A+ is an organic counterion.

The amount of use of the compound represented by formula (8) is about 1 to 2 moles based on the compound represented by formula (12). The salt of formula (1) thus obtained may be recovered, if obtained in a solid form, after purification by a recrystallization method, or a solidification method using a mixture of a good solvent and a poor solvent for the salt. If the salt is obtained in an oily form, the salt may be recovered after extraction with a solvent, or concentration.

As an example of the method for producing the compound of formula (8), a method of reacting an alcohol represented by the following formula (10) with carbonyl chloride represented by the following formula (11) may be used:

[Formula 10]

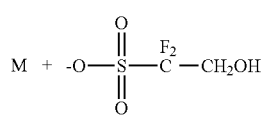

[Formula 11]

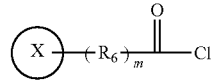

In the formula (10), M is Li, Na or K. In the formula (11), ring X represents a monocyclic or polycyclic hydrocarbon group having 3 to 30 carbon atoms, and having at least one hydrogen atom on the ring substituted by an alkyl or alkoxy group which has 1 to 10 carbon atoms and may be unsubstituted or substituted with a group selected from an ether group, an ester group, a carbonyl group, an acetal group, an epoxy group, a nitrile group and an aldehyde group, or by a perfluoroalkyl group having 1 to 4 carbon atoms, a hydroxyalkyl group having 1 to 10 carbon atoms, or a cyano group; $R_6$ is an alkyl group having 1 to 10 carbon atoms, an alkoxy group having 1 to 10 carbon atoms, or a heteroatom selected from the group consisting of N, S and F; and m is an integer from 0 to 2.

Specifically, in this method, an alcohol represented by the formula (10) and carbonyl chloride represented by the formula (11) are dissolved in a reaction solvent such as dichloromethane, chloroform, dichloroethane, acetonitrile or toluene generally at a temperature of 0 to 100° C., and then the dissolved reactants are allowed to react in the presence of a basic catalyst such as triethylamine, diethylamine, pyridine or diethylisopropylamine in an amount of about 1 to 2 moles based on the reactant of formula (11), or in the presence of N,N-dimethylaminopyridine as a catalyst in an amount of 0.1 to 0.5 moles based on the total amount of reactants.

In an exemplary method for producing the alcohol of formula (10), an ester compound represented by the following formula (9) is dissolved in tetrahydrofuran and an alcoholic solvent such as methanol, ethanol or propanol, and reducing agent is slowly added dropwise to the solution in an ice bath. After completion of the dropwise addition, the reaction mixture is stirred in an oil bath at 60° C. for about 4 hours, and then is quenched with distilled water to remove the solvents. The reaction mixture which is now free of solvent, is dissolved again in distilled water, and then the mixture is acidified to pH 5 to 6 using concentrated hydrochloric acid. The resulting mixture is concentrated, and then methanol is added thereto to form a slurry. The slurry is filtered, and the filtrate is washed with hexane, concentrated again, and is subjected to crystallization from diethyl ether. The obtained crystals is then filtered and dried to give the alcohol of formula (10).

[Formula 9]

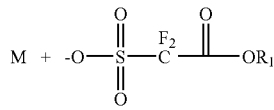

wherein $R_1$ is selected from the group consisting of hydrogen, methyl, trifluoromethyl, trichloromethyl, tribromomethyl and triiodomethyl; and M is Li, Na or K.

The acid generating agent according to embodiments of the present invention, which is formed by introducing an alicyclic ring into an anion, has advantages of being capable of controlling the diffusion rate of acid, exhibiting high light transmissibility when used in connection with an ArF light source.

The reducing agent is selected from sodium borohydride (NaBH4), lithium aluminum hydride (LiAlH4), BH3-THF, NaBH4-AlCl3, NaBH4-LiCl, and LiAl(OMe)$_3$.

BRIEF DESCRIPTION OF THE DRAWINGS

FIG. 1 is a $^1$H-NMR spectrum of the compound produced according to Synthesis Example 1-1;
FIG. 2 is a $^1$H-NMR spectrum of the compound produced according to Synthesis Example 1-2.

DESCRIPTION OF THE PREFERRED EMBODIMENTS

Figure 3:
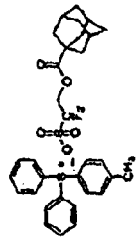
FIG. 3 is a $^1$H-NMR spectrum of the compound produced according to Synthesis Example 1-3.
Figure 3:
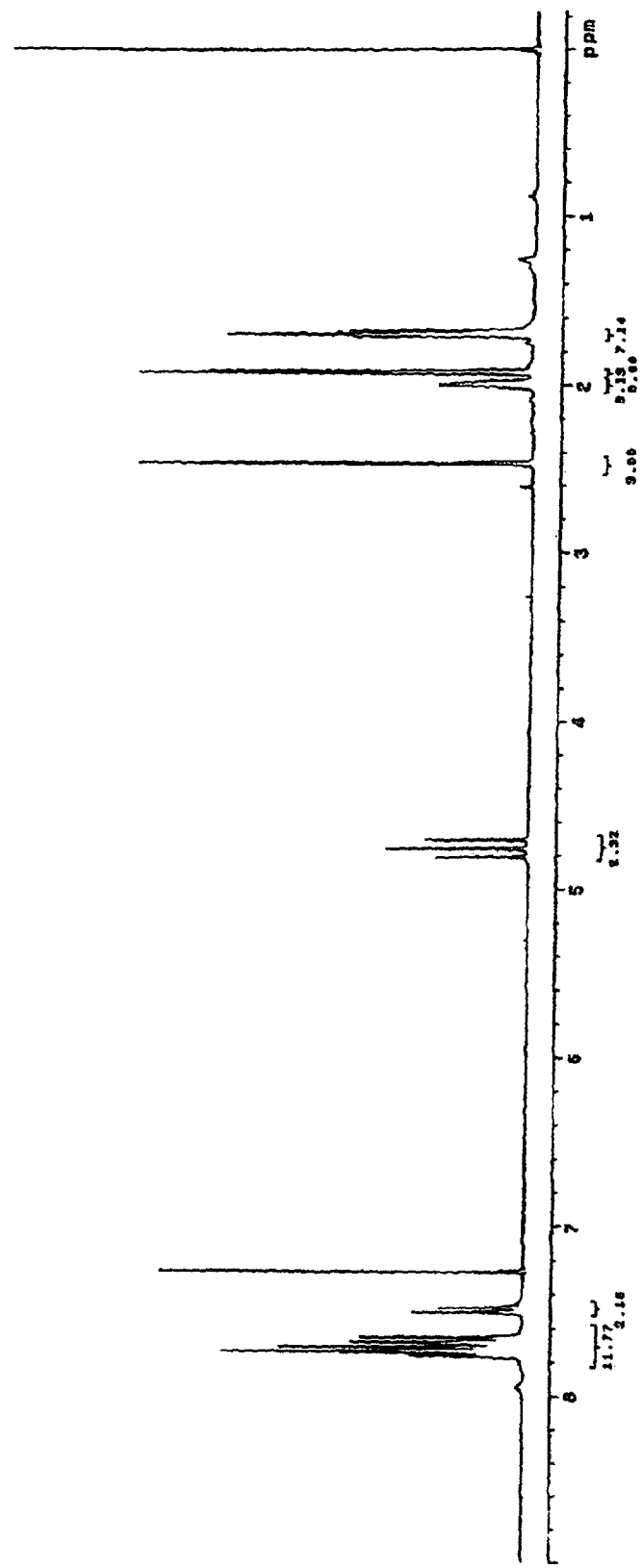

Hereinafter, the present invention will be described in detail with reference to preferred Synthesis Examples and Examples. However, it should be noted that the present invention is not intended to be limited to these Examples.

Synthesis Example 1

Adamantane-1-carboxylic acid 2,2-difluoro-2-sulfoethyl ester diphenyl methylphenyl sulfonium salt (1) 83 g of difluorosulfoacetic acid ethyl ester sodium salt is dissolved in 160 ml of methanol and 1.2 L of tetra hydrofuran (THF) in an ice bath, and 44 g of sodium borohydride (NaBH$_4$) is slowly added dropwise to the solution. After completion of the dropwise addition, the ice bath is removed, and the system temperature is elevated to 60° C., at which temperature the reaction system is stirred for about 4 hours.

When the reaction is completed, the reaction mixture is quenched with distilled water, and then the solvent is removed. The crude reaction mixture is dissolved again in distilled water, and is acidified to pH 5 to 6 using concentrated hydrochloric acid. Subsequently, methanol is added to the concentrated mixture, and the slurry thus formed is filtered to remove inorganic salts. The filtrate is washed two times with hexane, the methanol layer is concentrated again, and then crystallization is performed using diethyl ether. The white solid obtained after the filtration is dried in vacuum, and the structure of the dried product is confirmed by $^1$H-NMR. The $^1$H-NMR spectrum of the obtained product is presented in FIG. 1. As such, 68.5 g (yield 95%) of difluorohydroxyethanesulfonic acid sodium salt was obtained.
$^1$H-NMR (D$_2$O): δ (ppm) 4.18 (t, 2H)

[Reaction formula]

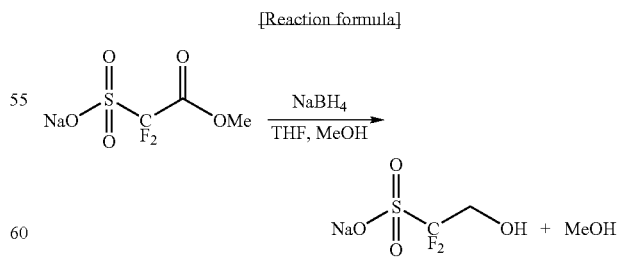

(2) 20 g of the difluorohydroxyethanesulfonic acid sodium salt produced as described above, and 29 g of adamantanecarbonyl chloride are dissolved in 400 ml of dichloroethane, and the solution is stirred at ambient temperature. 23 ml of triethylamine is slowly added dropwise to the solution at ambient temperature, and then the reaction temperature is elevated to 60° C., at which temperature the reaction system is stirred for 2 hours.

After completion of the reaction, the reaction solvent is removed, and ethyl ether is added to form a slurry. The slurry is filtered, and then filter cake is washed with distilled water and ethyl ether, and dried in vacuum. The structure of the dried product is confirmed by $^1$H-NMR. The $^1$H-NMR spectrum of the obtained product is presented in FIG. 2. As such, 30 g (yield 80%) of adamantane-1-carboxylic acid 2,2-difluoro-2-sulfoethyl ester sodium salt was obtained.

$^1$H-NMR (DMSO-$d_6$, internal standard: tetramethylsilane) δ (ppm) 1.67-1.98 (m, 15H), 4.52 (t, 2H)

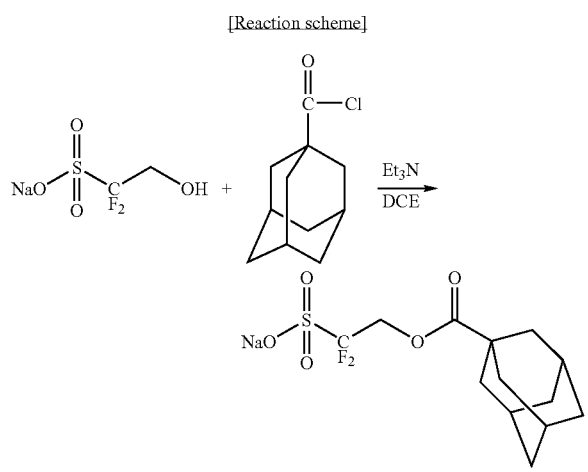

(3) 8.5 g of the adamantane-1-carboxylic acid 2,2-difluoro-2-sulfoethyl ester sodium salt produced in (2), and 10 g of diphenyl methylphenyl sulfonium trifluoromethanesulfonate are dissolved in 100 ml of dichloromethane and 100 ml of water, and the system is allowed to undergo a two-layer reaction with vigorous stirring for 3 hours.

After completion of the stirring, an aliquot of the organic layer is removed, and the progress of the reaction is checked by $^{19}$F-NMR. When the reaction goes to completion, the organic layers are combined, the solvent is removed, and the residues are washed with dichloromethane which is a good solvent, and with hexane which is a poor solvent. The solvents are removed, and the residues are dried under reduced pressure. Thus, 13.3 g (yield 94.3%) of adamantane-1-carboxylic acid 2,2-difluoro-2-sulfoethyl ester diphenyl fluorophenyl sulfonium salt was obtained, and the structure of the product was confirmed by $^1$H-NMR. The obtained spectrum is presented in FIG. 3.

$^1$H-NMR (chloroform-$d_3$, internal standard: tetramethylsilane): δ (ppm) 1.67-1.98 (m, 15H), 2.47 (s, 3H), 4.76 (t, 2H), 7.48 (d, 2H), 7.65-7.76 (m, 12H)

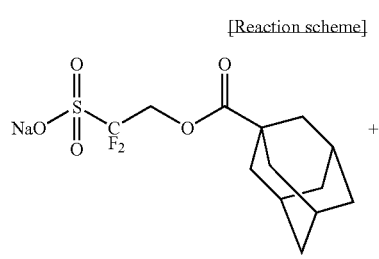

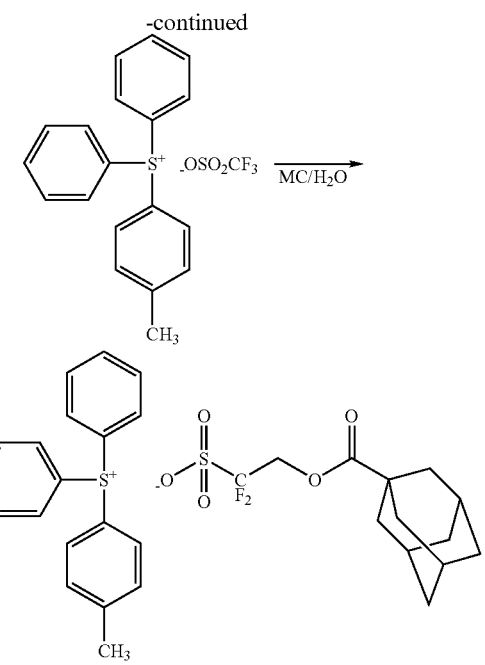

Synthesis Example 2

(1) 10 g of the difluorohydroxyethanesulfonic acid sodium salt produced in Synthesis Example 1-(1), and 8.7 ml of cyclohexanecarbonyl chloride are dissolved in 400 ml of dichloroethane, and the system is stirred at ambient temperature. 23 ml of triethylamine is slowly added dropwise at ambient temperature, and then the reaction temperature is elevated to 60° C., at which temperature the reaction system is stirred for 2 hours.

Figure 4:
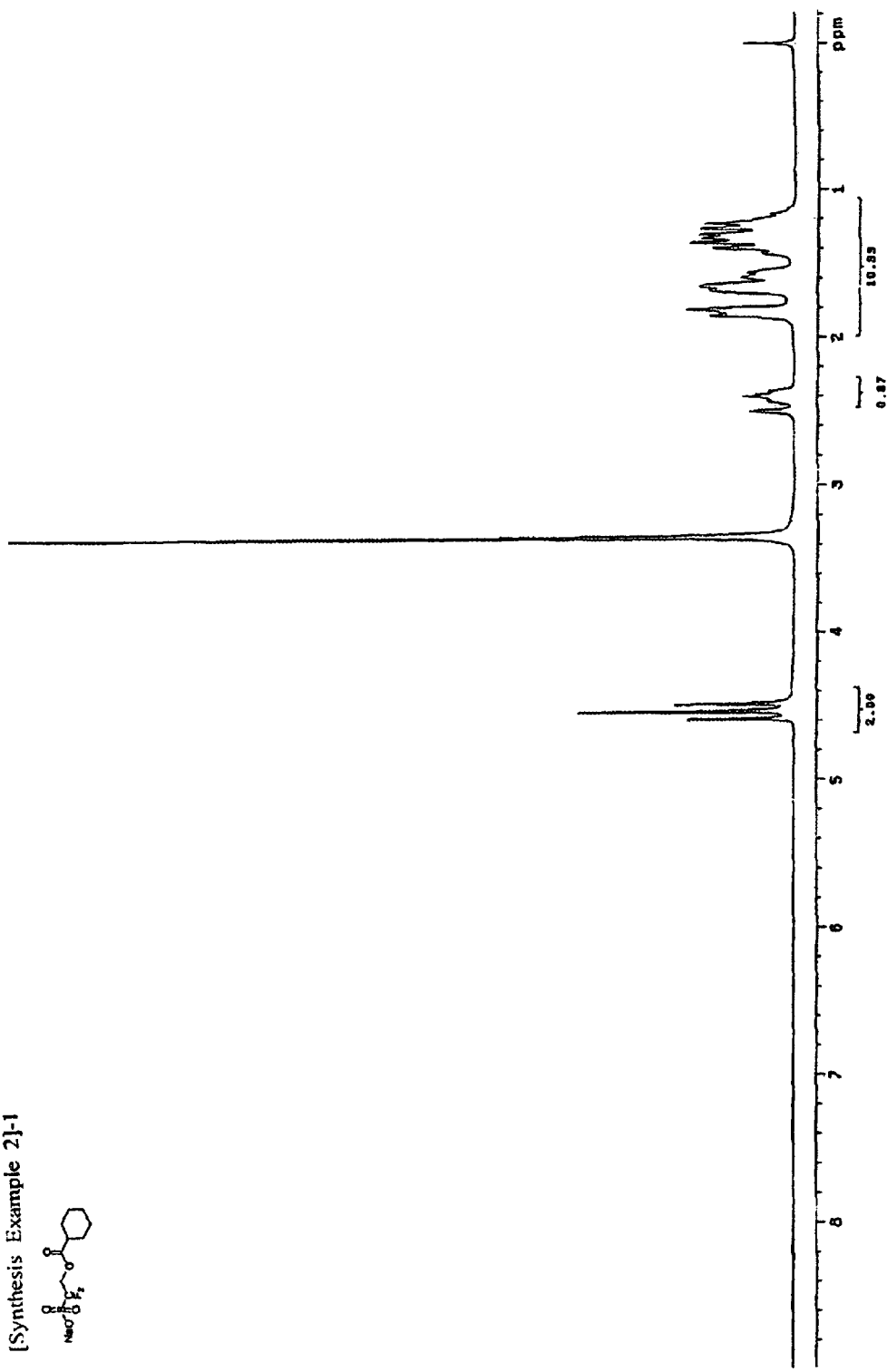
FIG. 4 is a $^1$H-NMR spectrum of the compound produced according to Synthesis Example 2-1.

After completion of the reaction, the reaction solvent is removed, and ethyl ether is added to form a slurry. The slurry is filtered, and then filter cake is washed with distilled water and ethyl ether, and dried in vacuum. The structure of the dried product is confirmed by $^1$H-NMR. The $^1$H-NMR spectrum of the obtained product is presented in FIG. 4. As such, 12.9 g (yield 81.2%) of cyclohexanecarboxylic acid 2,2-difluoro-2-sulfoethyl ester sodium salt having a structure as shown below was obtained.

$^1$H-NMR (DMSO-$d_6$, internal standard: tetramethylsilane): δ (ppm) 1.21-1.92 (m, 10H), 2.40 (m, 1H), 4.52 (t, 2H)

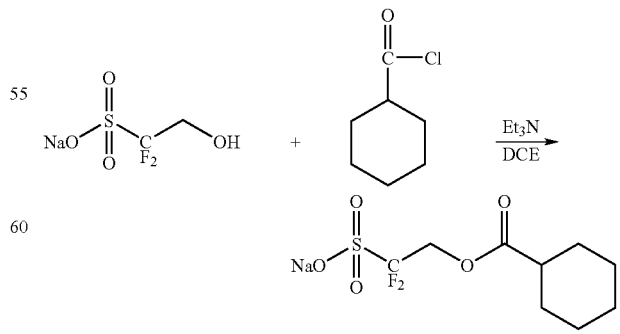

(2) 8.3 g of the cyclohexanecarboxylic acid-2,2-difluoro-2-sulfoethyl ester sodium salt produced in (1), and 10 g of diphenyl methylphenyl sulfonium trifluoromethanesulfonate are dissolved in 100 ml of dichloromethane and 100 ml of water, and the system is allowed to undergo a two-layer reaction with vigorous stirring for 3 hours.

Figure 5:
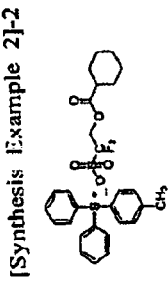
FIG. 5 is a $^1$H-NMR spectrum of the compound produced according to Synthesis Example 2-2.
Figure 5:
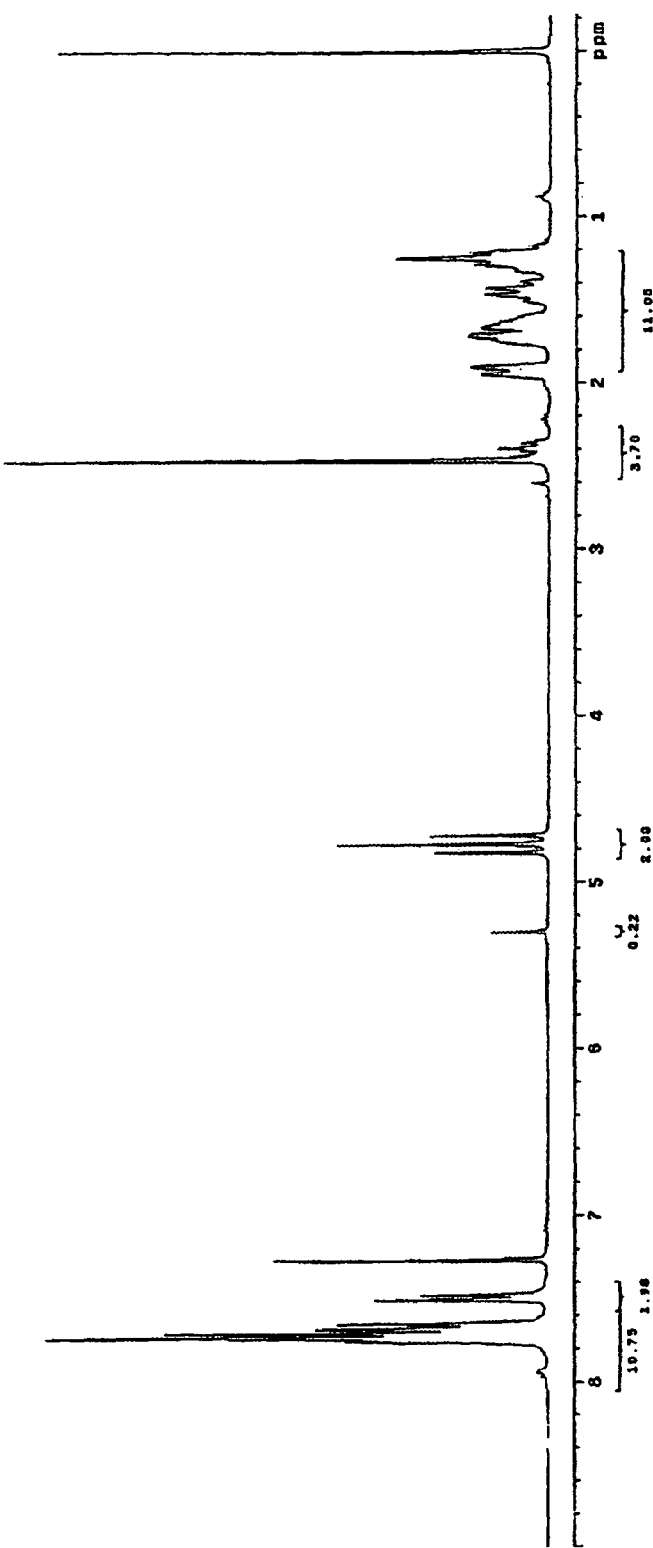

After completion of the stirring, an aliquot of the organic layer is removed, and the progress of the reaction is checked by $^{19}$F-NMR. When the reaction goes to completion, the organic layers are combined, the solvent is removed, and the residues are washed with dichloromethane which is a good solvent, and with hexane which is a poor solvent. The solvents are removed, and the residues are dried under reduced pressure. Thus, 12 g (yield 95.2%) of cyclohexanecarboxylic acid 2,2-difluoro-2-sulfoethyl ester diphenyl methylphenyl sulfonium salt was obtained, and the structure of the product was confirmed by $^1$H-NMR. The obtained spectrum is presented in FIG. 5.

$^1$H-NMR (chloroform-d$_3$, internal standard: tetramethylsilane): δ (ppm) 1.18-2.05 (m, 10H), 2.42 (m, 1H), 2.46 (s, 3H), 4.77 (t, 2H), 7.48 (d, 2H), 7.65-7.76 (m, 12H)

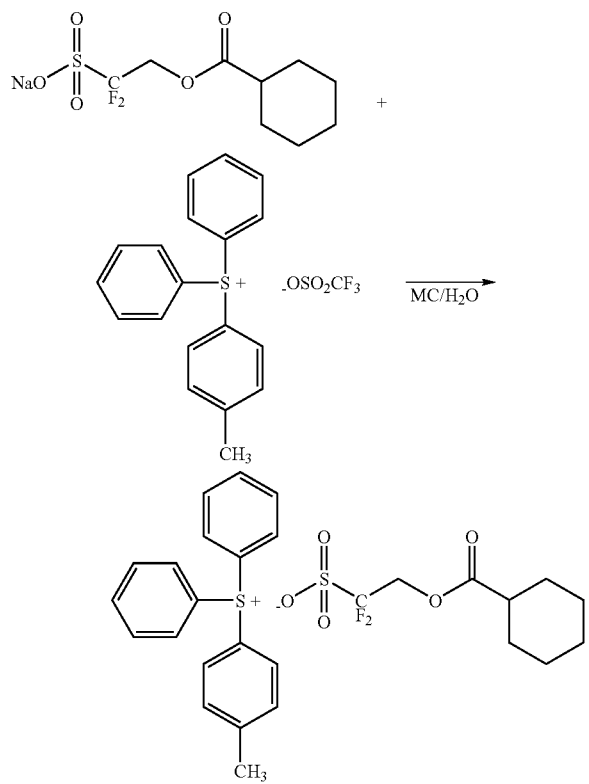

Synthesis Example 3

(1) 20 g of the difluorohydroxyethanesulfonic acid sodium salt produced in Synthesis Example 1-(1), and 26 g of nor-bornanecarbonyl chloride are dissolved in 400 ml of dichloroethane, and the system is stirred at ambient temperature. 30.4 ml of triethylamine is slowly added dropwise at ambient temperature, and then the reaction temperature is elevated to 60° C., at which temperature the reaction system is stirred for 2 hours.

Figure 6:
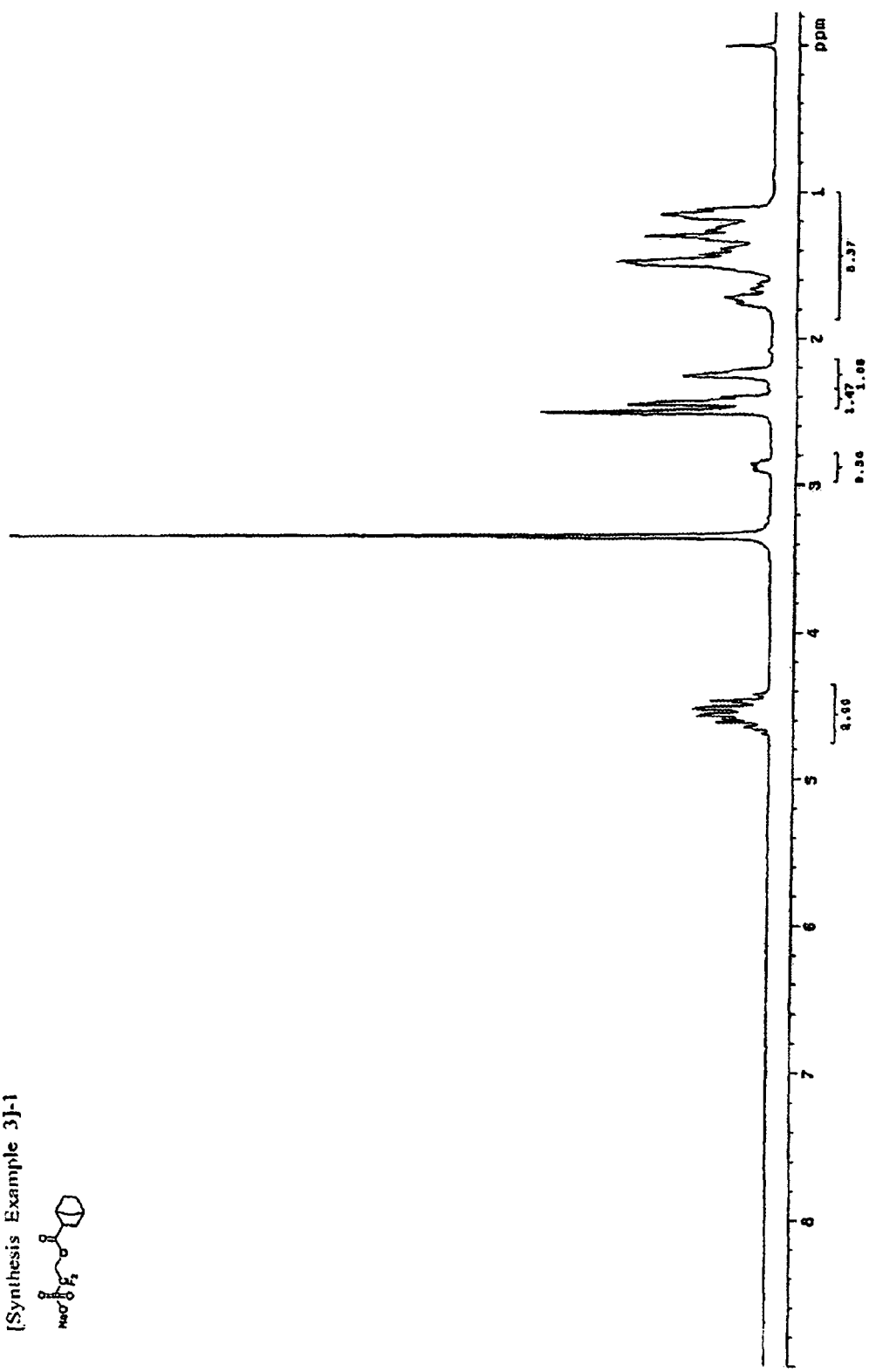
FIG. 6 is a $^1$H-NMR spectrum of the compound produced according to Synthesis Example 3-1.

After completion of the reaction, the reaction solvent is removed, and ethyl ether is added to form a slurry. The slurry is filtered, and then filter cake is washed with distilled water and ethyl ether, and dried in vacuum. The structure of the dried product is confirmed by $^1$H-NMR. The $^1$H-NMR spectrum of the obtained product is presented in FIG. 6. As such, 28.9 g (yield 86.2%) of bicyclo[2.2.1]heptane-2-carboxylic acid 2,2-difluoro-2-sulfoethyl ester sodium salt having a structure as shown below was obtained.

$^1$H-NMR (DMSO-d$_6$, internal standard: tetramethylsilane) δ (ppm) 1.15-2.82 (m, 1H), 4.57 (m, 2H)

[Reaction scheme]

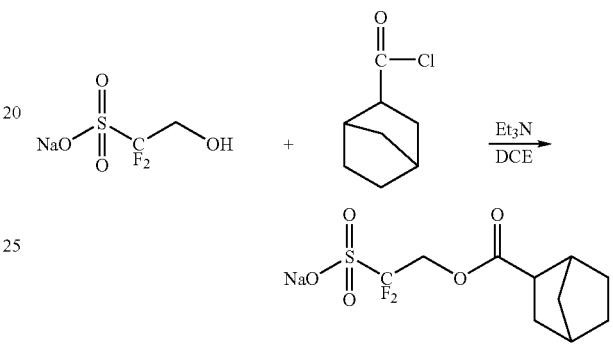

(2) 15.1 g of the bicyclo[2.2.1]heptane-2-carboxylic acid 2,2-difluoro-2-sulfoethyl ester sodium salt produced in (1), and 15 g of diphenyl methylphenyl sulfonium trifluoromethanesulfonate are dissolved in 150 ml of dichloromethane and 150 ml of water, and the system is allowed to undergo a two-layer reaction with vigorous stirring for 3 hours.

Figure 7:
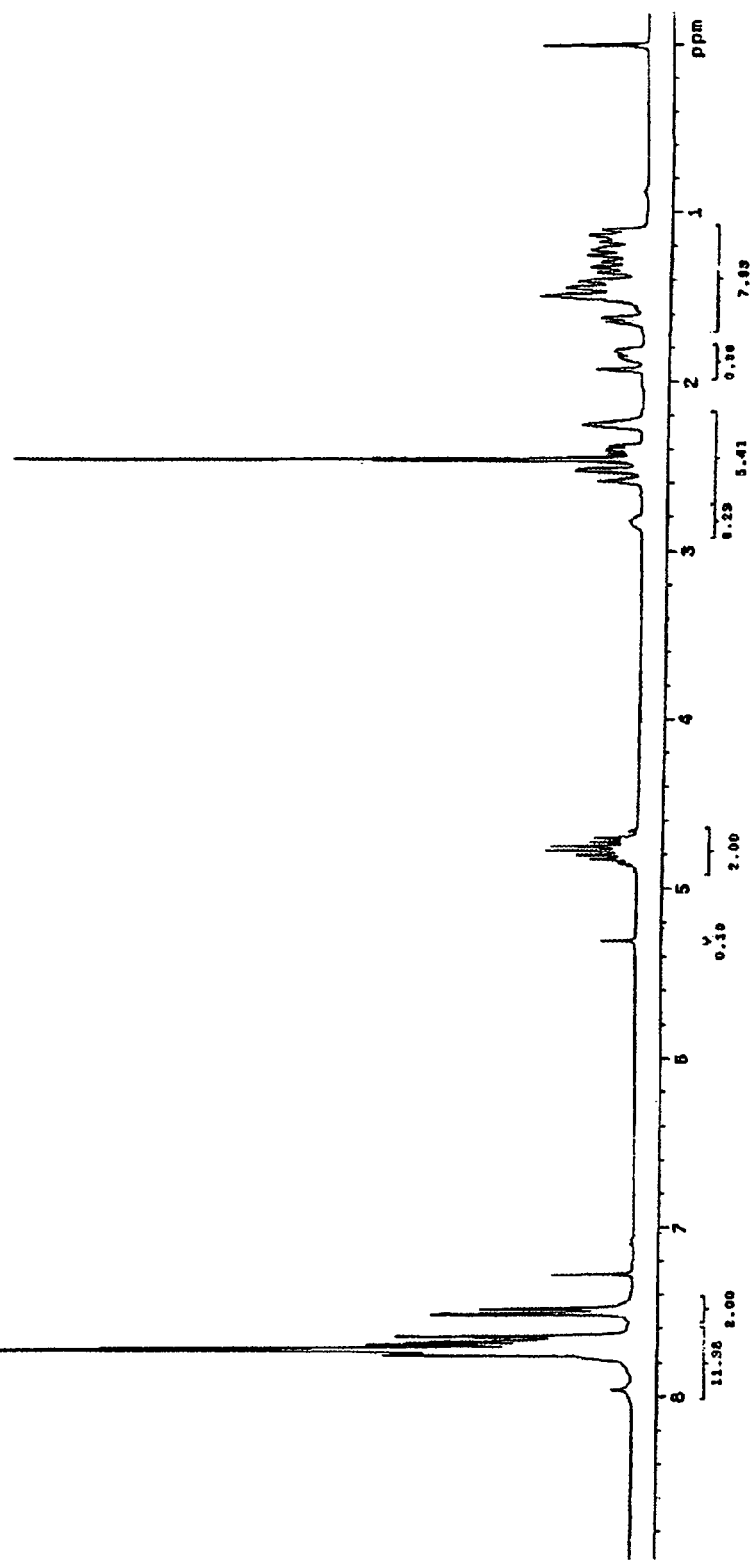
FIG. 7 is a $^1$H-NMR spectrum of the compound produced according to Synthesis Example 3-2.

After completion of the stirring, an aliquot of the organic layer is removed, and the progress of the reaction is checked by $^{19}$F-NMR. When the reaction goes to completion, the organic layers are combined, the solvent is removed, and the residues are washed with dichloromethane which is a good solvent, and with hexane which is a poor solvent. The solvents are removed, and the residues are dried under reduced pressure. Thus, 18.8 g (yield 95.2%) of bicyclo[2.2.1]heptane-2-carboxylic acid 2,2-difluoro-2-sulfoethyl ester diphenyl methylphenyl sulfonium salt was obtained, and the structure of the product was confirmed by $^1$H-NMR. The obtained spectrum is presented in FIG. 7.

$^1$H-NMR (chloroform-d$_3$, internal standard: tetramethylsilane): δ (ppm) 1.51-2.84 (m, 11H), 2.46 (s, 3H), 4.77 (m, 2H), 7.48 (d, 2H), 7.65-7.76 (m, 12H)

[Reaction scheme]

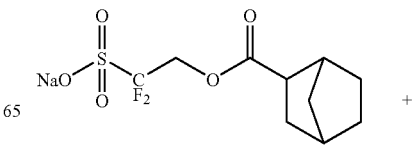

-continued

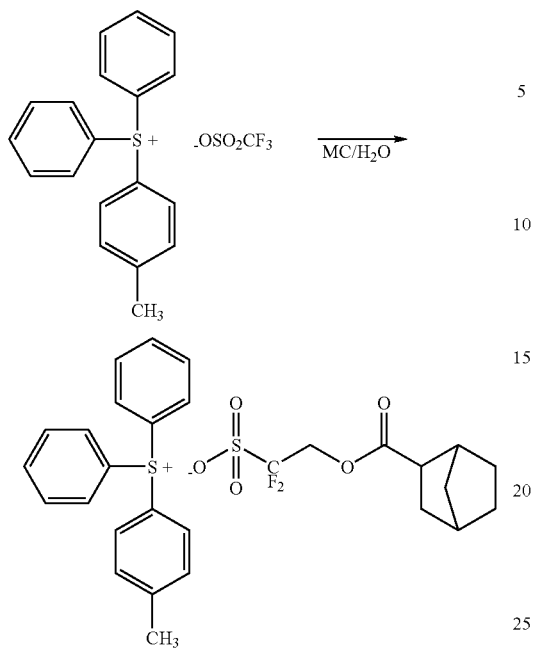

-continued

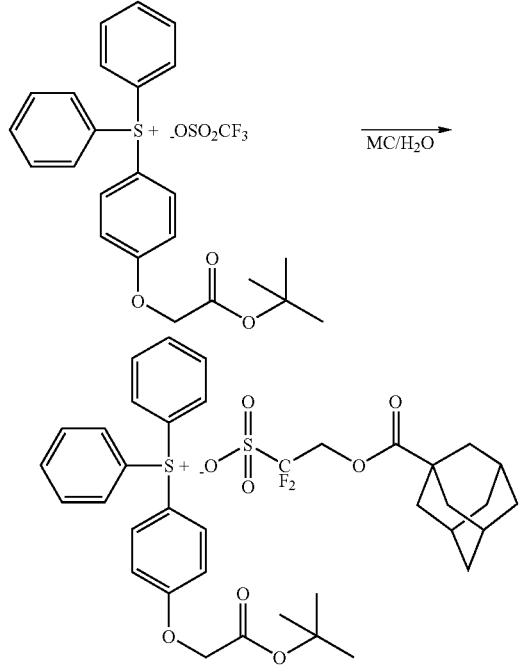

Synthesis Example 4

(1) 7 g of the adamantane-1-carboxylic acid 2,2-difluoro-2-sulfoethyl ester sodium salt produced in Synthesis Example 1-(2), and 10 g of diphenyl t-butoxycarbonylmethoxyphenyl sulfonium trifluoromethanesulfonate are dissolved in 100 ml of dichloromethane and 100 ml of water, and the system is allowed to undergo a two-layer reaction with vigorous stirring for 3 hours.

Figure 8:
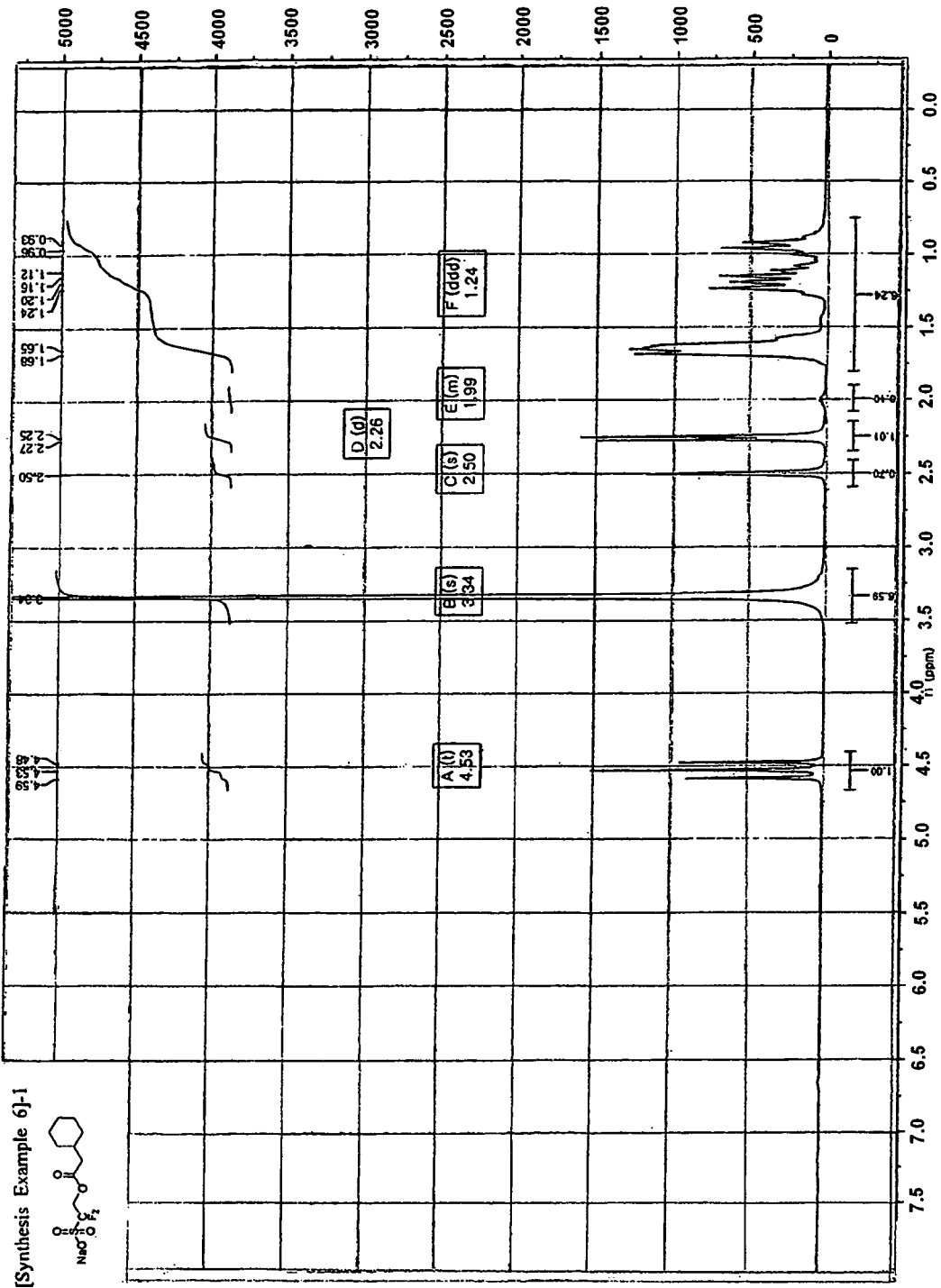
FIG. 8 is a $^1$H-NMR spectrum of the compound produced according to Synthesis Example 6-1.

After completion of the stirring, an aliquot of the organic layer is removed, and the progress of the reaction is checked by $^{19}$F-NMR. When the reaction goes to completion, the organic layers are combined, the solvent is removed, and the residues are washed with dichloromethane which is a good solvent, and with hexane which is a poor solvent. The solvents are removed, and the residues are dried under reduced pressure. Thus, 12.2 g (yield 94.6%) of adamantane-1-carboxylic acid 2,2-difluoro-2-sulfoethyl ester diphenyl t-butoxycarbonylmethoxyphenyl sulfonium salt was obtained, and the structure of the product was confirmed by $^1$H-NMR. The obtained spectrum is presented in FIG. 8.

$^1$H-NMR (chloroform-d$_3$, internal standard: tetramethylsilane): δ (ppm) 1.48 (s, 9H), 1.67-1.98 (m, 15H), 2.47 (s, 3H), 4.62 (s, 2H), 4.76 (t, 2H), 7.17 (d, 2H), 7.65-7.77 (m, 12H)

Synthesis Example 5

(1) 8.9 g of the adamantane-1-carboxylic acid 2,2-difluoro-2-sulfoethyl ester sodium salt produced in Synthesis Example 1-(2), and 10 g of diphenyl fluorophenyl sulfonium trifluoromethanesulfonate are dissolved in 100 ml of dichloromethane and 100 ml of water, and the system is allowed to undergo a two-layer reaction with vigorous stirring for 3 hours.

Figure 9:
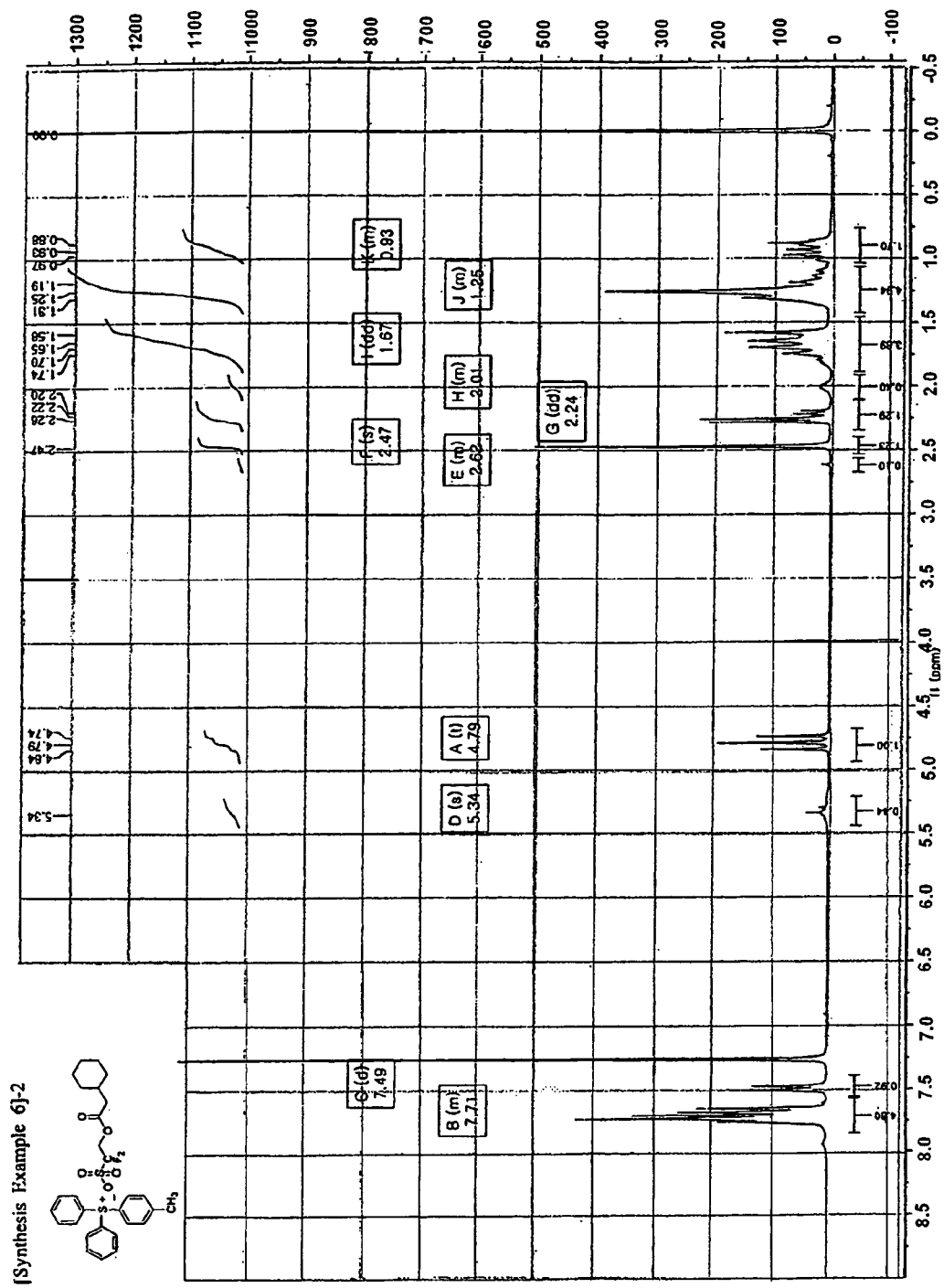
FIG. 9 is a $^1$H-NMR spectrum of the compound produced according to Synthesis Example 6-2.

After completion of the stirring, an aliquot of the organic layer is removed, and the progress of the reaction is checked by $^{19}$F-NMR. When the reaction goes to completion, the organic layers are combined, the solvent is removed, and the residues are washed with dichloromethane which is a good solvent, and with hexane which is a poor solvent. The solvents are removed, and the residues are dried under reduced pressure. Thus, 12.8 g (yield 92.1%) of adamantane-1-carboxylic acid 2,2-difluoro-2-sulfoethyl ester diphenyl fluorophenyl sulfonium salt was obtained, and the structure of the product was confirmed by $^1$H-NMR. The obtained spectrum is presented in FIG. 9.

$^1$H-NMR (chloroform-d$_3$, internal standard: tetramethylsilane): δ (ppm) 1.67-1.98 (m, 15H), 4.76 (t, 2H), 7.36-7.91 (m, 14H)

[Reaction Scheme]

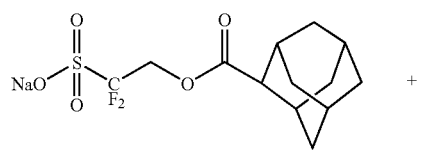

[Reaction Scheme]

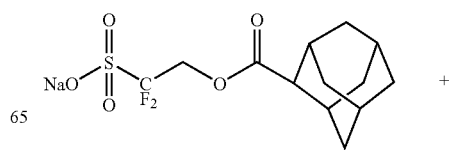

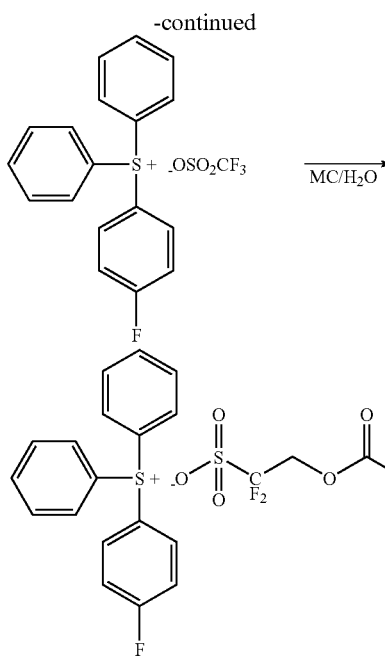

Figure 11:
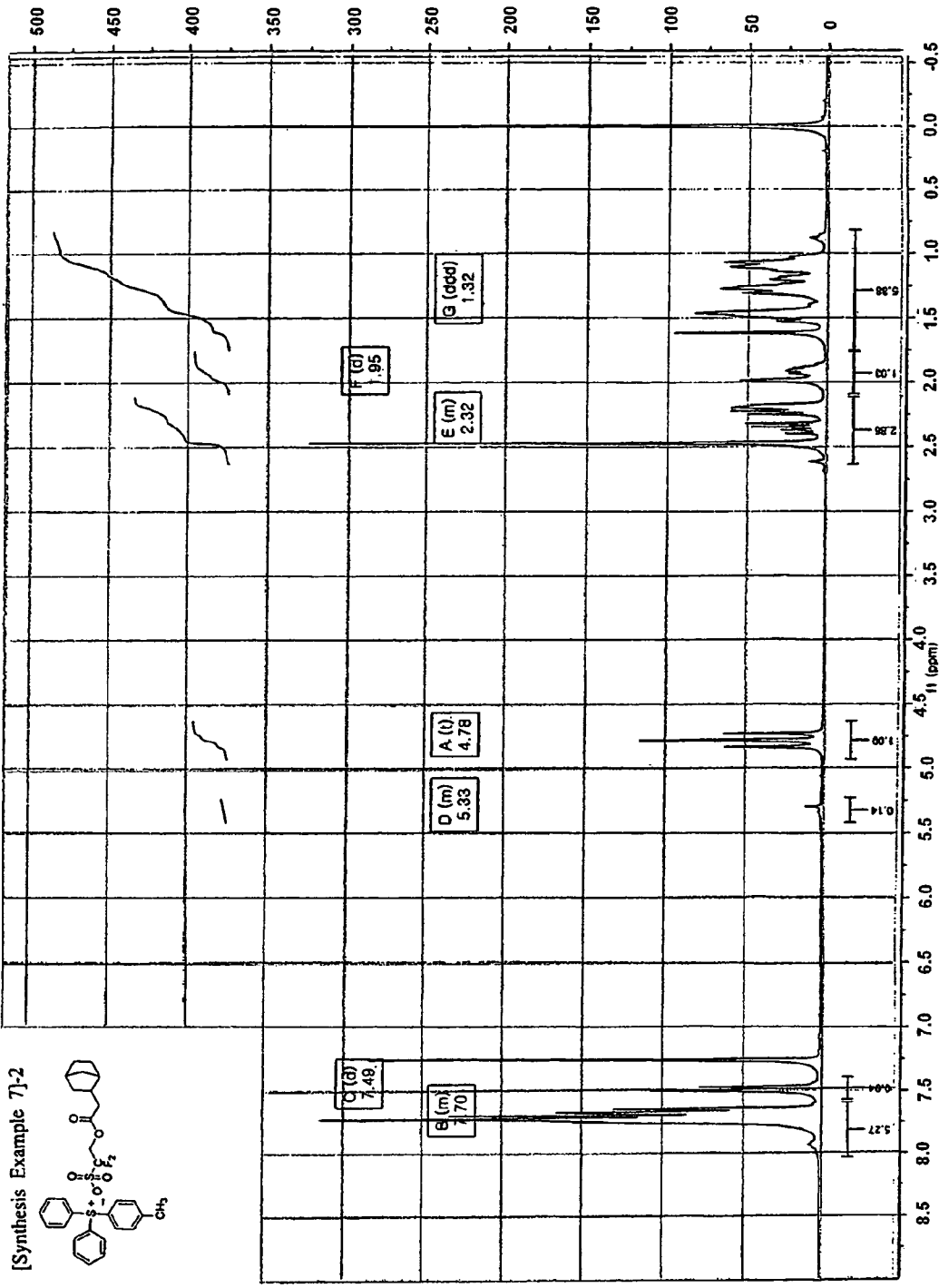
FIG. 11 is a $^1$H-NMR spectrum of the compound produced according to Synthesis Example 7-2.

After completion of the stirring, an aliquot of the organic layer is removed, and the progress of the reaction is checked by $^{19}$F-NMR. When the reaction goes to completion, the organic layers are combined, the solvent is removed, and the residues are washed with dichloromethane which is a good solvent, and with hexane which is a poor solvent. The solvents are removed, and the residues are dried under reduced pressure. Thus, 11.6 g (yield 98.1%) of cyclohexylacetic acid 2,2-difluoro-2-sulfoethyl ester diphenyl methylphenyl sulfonium salt was obtained, and the structure of the product was confirmed by $^1$H-NMR. The obtained spectrum is presented in FIG. 11.

$^1$H-NMR (chloroform-d$_3$, internal standard: tetramethylsilane): δ (ppm) 0.82-1.67 (m, 11H), 2.24 (d, 2H), 2.62 (s, 3H), 4.79 (t, 2H), 7.49 (d, 2H), 7.65-7.76 (m, 12H)

[Reaction scheme]

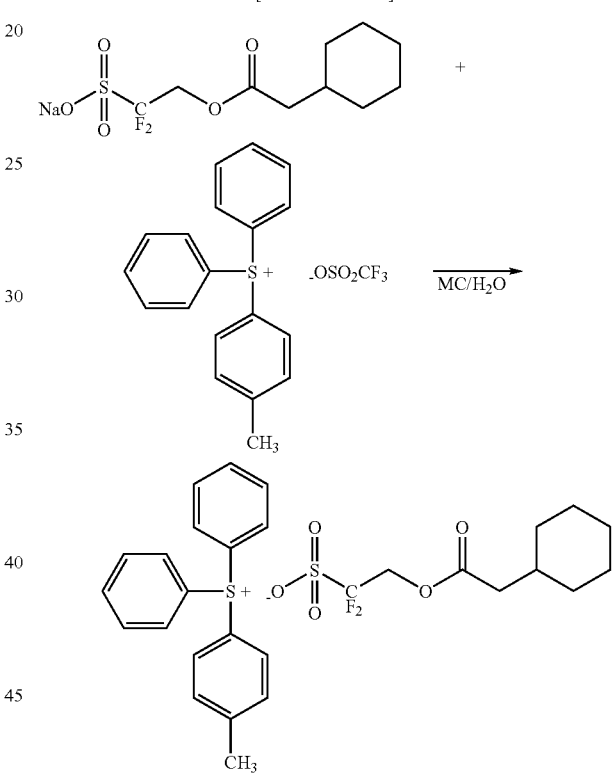

Synthesis Example 6

(1) 10 g of the difluorohydroxyethanesulfonic acid sodium salt produced in Synthesis Example 1-(1), and 10.5 ml of cyclohexaneacetyl chloride are dissolved in 150 ml of dichloroethane, and the system is stirred at ambient temperature. 11 ml of triethylamine is slowly added dropwise at ambient temperature, and then the reaction system is stirred for 12 hours at ambient temperature.

Figure 10:
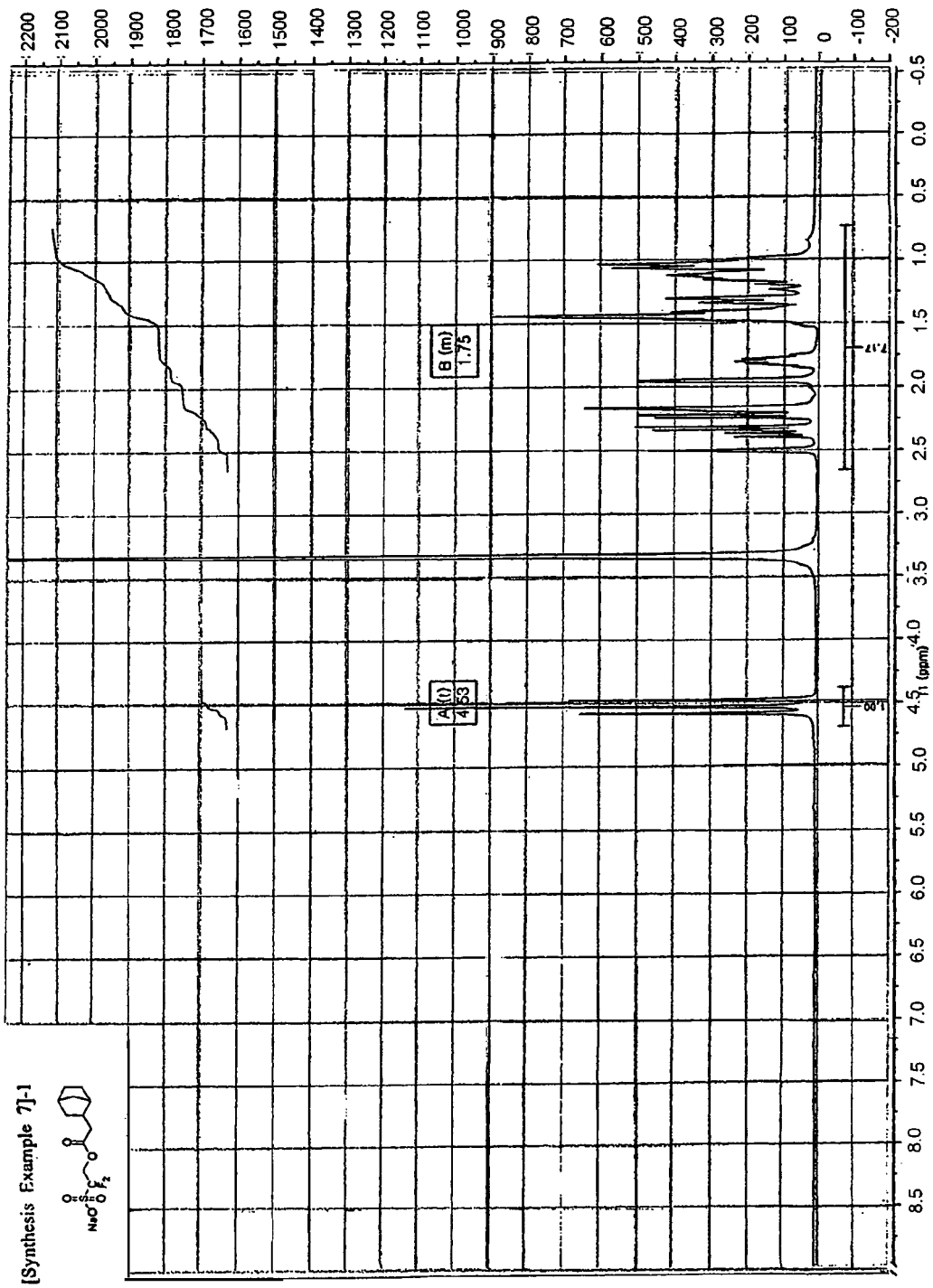
FIG. 10 is a $^1$H-NMR spectrum of the compound produced according to Synthesis Example 7-1.

After completion of the reaction, the reaction solvent is removed, and ethyl ether is added to form a slurry. The slurry is filtered, and then filter cake is washed with distilled water and ethyl ether, and dried in vacuum. The structure of the dried product is confirmed by $^1$H-NMR. The $^1$H-NMR spectrum of the obtained product is presented in FIG. 10. As such, 15 g (yield 89.6%) of cyclohexylacetic acid 2,2-difluoro-2-sulfoethyl ester sodium salt having a structure as shown below was obtained.

$^1$H-NMR (DMSO-d$_6$, internal standard: tetramethylsilane): δ (ppm) 0.82-1.75 (m, 1H), 2.26 (d, 2H), 4.53 (t, 2H)

[Reaction scheme]

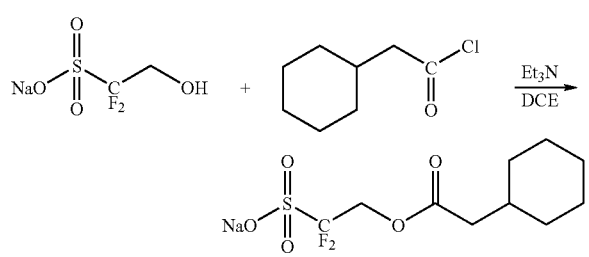

(2) 9.1 g of the cyclohexylacetic acid 2,2-difluoro-2-sulfoethyl ester sodium salt produced in (1), and 9 g of diphenyl methylphenyl sulfonium trifluoromethanesulfonate are dissolved in 90 ml of dichloromethane and 90 ml of water, and the system is allowed to undergo a two-layer reaction with vigorous stirring for 3 hours.

Synthesis Example 7

(1) 20 g of the difluorohydroxyethanesulfonic acid sodium salt produced in Synthesis Example 1-(1), and 28.3 g of norbornaneacetyl chloride are dissolved in 400 ml of dichloroethane, and the system is stirred at ambient temperature. 30.4 ml of triethylamine is slowly added dropwise at ambient temperature, and then the reaction temperature is elevated to 60° C., at which temperature the reaction system is stirred for 2 hours.

After completion of the reaction, the reaction solvent is removed, and ethyl ether is added to form a slurry. The slurry is filtered, and then filter cake is washed with distilled water and ethyl ether, and dried in vacuum. The structure of the dried product is confirmed by $^1$H-NMR. The $^1$H-NMR spectrum of the obtained product is presented in FIG. 12. As such, 32 g (yield 91.7%) of bicyclo[2.2.1]heptane-2-acetic acid 2,2-difluoro-2-sulfoethyl ester sodium salt having a structure as shown below was obtained.

$^1$H-NMR (DMSO-d$_6$, internal standard: tetramethylsilane) δ (ppm) 0.81-2.42 (m, 13H), 4.53 (t, 2H)

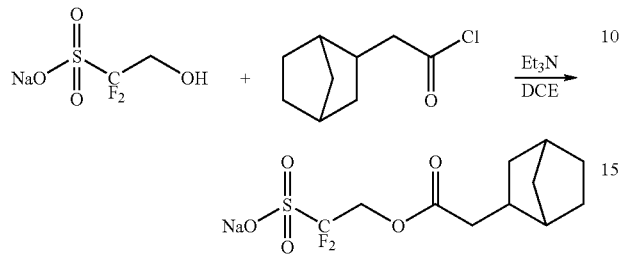

(2) 15.8 g of the bicyclo[2.2.1]heptane-2-acetic acid 2,2-difluoro-2-sulfoethyl ester sodium salt produced in (2), and 15 g of diphenyl methylphenyl sulfonium trifluoromethanesulfonate are dissolved in 150 ml of dichloromethane and 150 ml of water, and the system is allowed to undergo a two-layer reaction with vigorous stirring for 3 hours.

After completion of the stirring, an aliquot of the organic layer is removed, and the progress of the reaction is checked by $^{19}$F-NMR. When the reaction goes to completion, the organic layers are combined, the solvent is removed, and the residues are washed with dichloromethane which is a good solvent, and with hexane which is a poor solvent. The solvents are removed, and the residues are dried under reduced pressure. Thus, 17 g (yield 81.7%) of bicyclo[2.2.1]heptane-2-acetic acid 2,2-difluoro-2-sulfoethyl ester diphenyl methylphenyl sulfonium salt was obtained, and the structure of the product was confirmed by $^1$H-NMR. The obtained spectrum is presented in FIG. 13.

$^1$H-NMR (chloroform-d$_3$, internal standard: tetramethylsilane): δ (ppm) 0.81-2.18 (m, 13H), 2.32 (s, 3H), 4.78 (t, 2H), 7.49 (d, 2H), 7.65-7.76 (m, 12H)

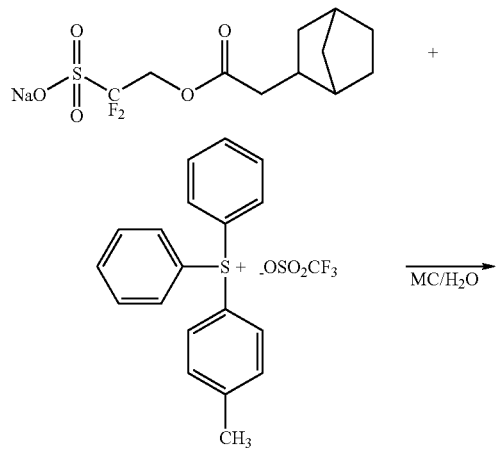

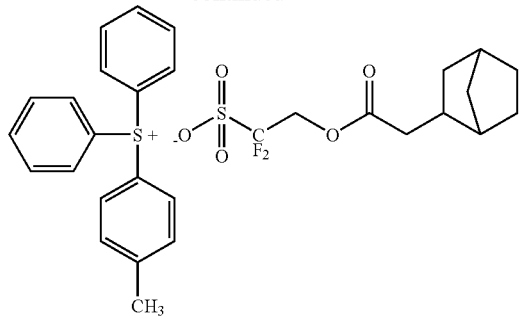

Synthesis Example 8

(1) 10 g of the difluorohydroxyethanesulfonic acid sodium salt produced in Synthesis Example 1-(1), and 12 g of adamantaneacetyl chloride are dissolved in 150 ml of dichloroethane, and the system is stirred at ambient temperature. 11 ml of triethylamine is slowly added dropwise at ambient temperature, and then the reaction system is stirred for 12 hours at ambient temperature.

After completion of the reaction, the reaction solvent is removed, and ethyl ether is added to form a slurry. The slurry is filtered, and then filter cake is washed with distilled water and ethyl ether, and dried in vacuum. The structure of the dried product is confirmed by $^1$H-NMR. The $^1$H-NMR spectrum of the obtained product is presented in FIG. 14. As such, 16 g (yield 79%) of adamantylacetic acid 2,2-difluoro-2-sulfoethyl ester sodium salt having a structure as shown below was obtained.

$^1$H-NMR (DMSO-d$_6$, internal standard: tetramethylsilane): δ (ppm) 0.82-1.75 (m, 11H), 2.26 (d, 2H), 4.53 (t, 2H)

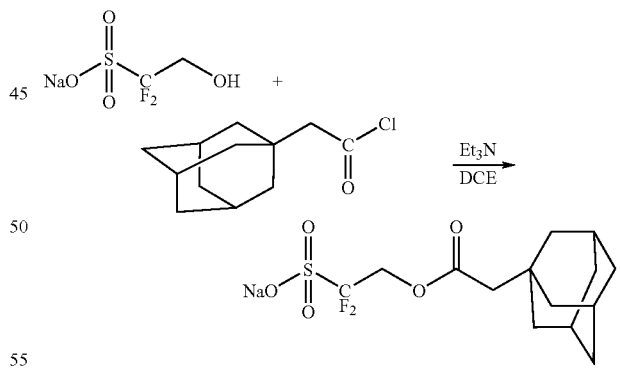

(2) 10 g of the adamantylacetic acid 2,2-difluoro-2-sulfoethyl ester sodium salt produced in (1), and 12 g of diphenyl methylphenyl sulfonium trifluoromethanesulfonate are dissolved in 90 ml of dichloromethane and 90 ml of water, and the system is allowed to undergo a two-layer reaction with vigorous stirring for 3 hours.

After completion of the stirring, an aliquot of the organic layer is removed, and the progress of the reaction is checked by $^{19}$F-NMR. When the reaction goes to completion, the organic layers are combined, the solvent is removed, and the residues are washed with dichloromethane which is a good solvent, and with hexane which is a poor solvent. The solvents are removed, and the residues are dried under reduced pressure. Thus, 20 g (yield 95%) of adamantylacetic acid 2,2-difluoro-2-sulfoethyl ester diphenyl methylphenyl sulfonium salt was obtained, and the structure of the product was confirmed by $^1$H-NMR. The obtained spectrum is presented in FIG. 15.

$^1$H-NMR (chloroform-$d_3$, internal standard: tetramethylsilane): δ (ppm) 0.81-2.18 (m, 13H), 2.32 (s, 3H), 4.78 (t, 2H), 7.49 (d, 2H), 7.65-7.76 (m, 12H)

[Reaction scheme]

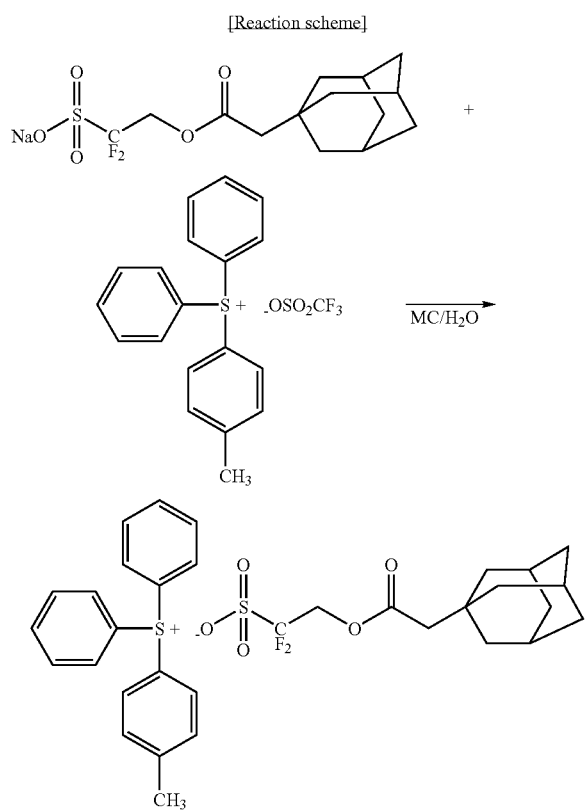

Resin Synthesis Example 1

3-Bicyclo[2.2.1]hept-5-en-2-yl-3-hydroxypropionic acid t-butyl ester (hereinafter, referred to as BHP), 1-methyladamantane acrylate and gamma-butyrolactone methyl acrylate are charged at a molar ratio of 1:1:1 (33 parts:33 parts:33 parts), and the mixture is allowed to react at 65° C. for 16 hours using 1,4-dioxane as a polymerization solvent in an amount of three-fold the total mass of the reaction monomers, and using azobisisobutyronitrile as an initiator in a proportion of 4% by mole based on the total molar amount of the monomers.

After the reaction, the reaction solution is immersed in n-hexane, and dried in vacuum to obtain the following resin. As a result, a copolymer having a weight average molecular weight of about 8,500 was obtained.

[Figure]

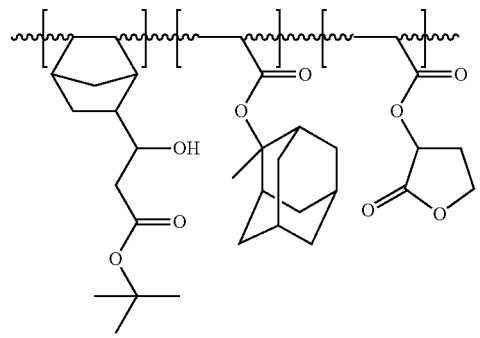

Preparation of Resist, Examples 1 to 3 and Comparative Example 1

Example 1

Preparation of Resist

To 100 parts by weight of the resin obtained in Resin Synthesis 1, 4 parts by weight of the adamantane-1-carboxylic acid 2,2-difluoro-2-sulfoethyl ester diphenyl methylphenyl sulfonium salt produced in Synthesis Example 1 as an acid generating agent, and 0.5 parts by weight of tetramethylammonium hydroxide as a basic additive were dissolved in 1,000 parts by weight of propylene glycol methyl ether acetate, and then the solution was filtered through a membrane filter having a pore size of 0.2 μm, to obtain a resist.

The obtained resist solution was applied on a substrate using a spinner, and dried at 110° C. for 90 seconds to form a coating film having a thickness of 0.20 μm. The formed film was exposed to an ArF excimer laser stepper (numerical aperture: 0.78), and then the film was heat treated at 110° C. for 90 seconds. Subsequently, development was performed with a 2.38 wt % aqueous solution of tetramethylammonium hydroxide for 40 seconds, and then washing and drying were performed to form a resist pattern.

The developability using an aqueous solution of tetramethylammonium hydroxide and the adhesiveness of the formed resist pattern to the substrate were good, and the resolution was 0.07 μm, while the sensitivity was 12 mJ/cm$^2$.

From the results of the Example, in the case of LER the pattern roughness of the 0.10 μm line-and-space (L/S) pattern formed after the development was observed, and the degree of improvement from the viewpoint of LER was graded from 1 to 5 (higher number corresponding to better LER), with the pattern obtained in Comparative Example being 1.

In the case of sensitivity, the amount of exposure for forming a 0.10 μm line-and-space (L/S) pattern formed after the development at a line width of 1:1, was designated as the optimum amount of exposure, and this optimum amount of exposure was taken as the sensitivity. The minimum pattern dimension obtained was taken as the resolution.

Examples 1 to 3

Each of the resins produced in the Resin Synthesis Example 1 using the PAG obtained in the Synthesis Examples 1, 2 and 3, and a basic additive were dissolved in 1,000 parts by weight of propylene glycol methyl ether acetate, and then the solution was filtered through a membrane filter having a pore size of 0.2 μm. Thus, the resist compositions shown in Table 1 (provided that the parts are parts by weight) were prepared. Positive resist patterns were formed by performing the same processes as in Example 1, and then various evaluations were performed. The evaluation results are presented in Table 1.

TABLE 1

| | Resin (100 parts by weight) | *PAG (parts by weight) | *Base (parts by weight) | Sensitivity (mJ/cm²) | Resolution (nm) | LER |
|---|---|---|---|---|---|---|
| Example 1 | Resin Synthesis Example 1 | 4.0 | 0.5 | 12 | 70 | 4 |
| Example 2 | Resin Synthesis Example 1 | 4.0 | 0.5 | 12 | 80 | 3 |
| Example 3 | Resin Synthesis Example 1 | 4.0 | 0.5 | 12 | 70 | 3 |
| Comparative Example 1 | Resin Synthesis Example 1 | 4.0 | 0.5 | 14 | 90 | 1 |

*Kind of PAG used in Table 1

Example 1

Adamantane-1-carboxylic acid 2,2-difluoro-2-sulfoethyl ester diphenyl methylphenyl sulfonium salt of Synthesis Example 1

Example 2

Cyclohexanecarboxylic acid 2,2-difluoro-2-sulfoethyl ester sodium salt of Synthesis Example 2

Example 3

Bicyclo[2.2.1]heptane-2-carboxylic acid 2,2-difluoro-2-sulfoethyl ester diphenyl methylphenyl sulfonium salt Comparative Example 1

Triphenylsulfonium Triflate

What is claimed is:

1. An acid generating agent represented by the following formula (1):

[Formula 1]

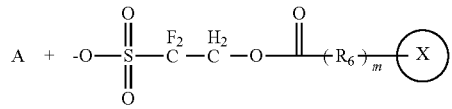

wherein X represents a monocyclic or polycyclic hydrocarbon group having 3 to 30 carbon atoms, and having at least one hydrogen atom substituted by an alkyl or alkoxy group which has 1 to 10 carbon atoms and may be unsubstituted or substituted with an ether group, an ester group, a carbonyl group, an acetal group, an epoxy group, a nitrile group or an aldehyde group, or by a perfluoroalkyl group having 1 to 4 carbon atoms, a hydroxyalkyl group having 1 to 10 carbon atoms or a cyano group; $R_6$ represents an alkyl group 1 to 10 carbon atoms, an alkoxy group having 1 to 10 carbon atoms, or a heteroatom selected from the group consisting of nitrogen (N) and sulfur (S); m is an integer from 1 to 2; and A+ is an organic counterion.

2. The acid generating agent according to claim 1, wherein X represents an adamantyl group, a norbornyl group or a cycloalkyl group.

3. The acid generating agent according to claim 1, wherein X is selected from the group consisting of the compounds of the following formulas (1-a) to (1-h):

[Formulas 1-a to 1-h]

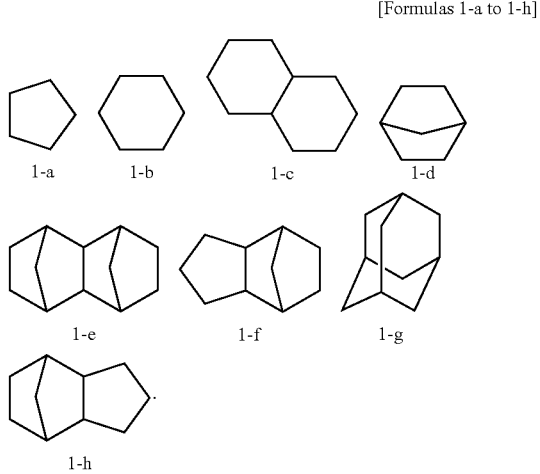

4. The acid generating agent according to claim 1, wherein A+ comprises a cation represented by the following formula (2a) or (2b):

[Formula 2a]

[Formula 2b]

wherein $R_1$ and $R_2$ each independently represent an alkyl group, an allyl group, a perfluoroalkyl group, a benzyl group or an aryl group; and $R_3$, $R_4$ and $R_5$ each independently represent a hydrogen atom, an alkyl group, a halogen atom, an alkoxy group, an aryl group, a thiophenoxy group, a thioalkoxy group or an alkoxycarbonylmethoxy group.

5. The acid generating agent according to claim 1, wherein A+ comprises a cation represented by the following formula (3a) or (3b):

[Formula 3a]

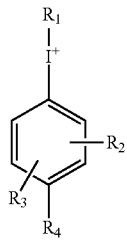

[Formula 3b]

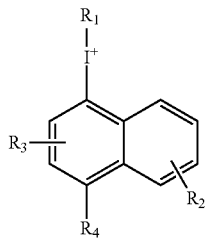

wherein $R_1$ and $R_4$ each independently represent an alkyl group, an allyl group, a perfluoroalkyl group, a benzyl group or an aryl group; and $R_2$ and $R_3$ each independently represent a hydrogen atom, an alkyl group, a halogen group, an alkoxy group, an aryl group, a thiophenoxy group, a thioalkoxy group or an alkoxycarbonylmethoxy group.

6. The acid generating agent according to claim 4, wherein the compound of the formula (2a) or (2b) is selected from the group consisting of the compounds of the following formulas (2-i) to (2-xx):

[Formulas 2-i to 2-xx]

2-i

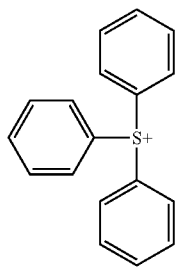

2-ii

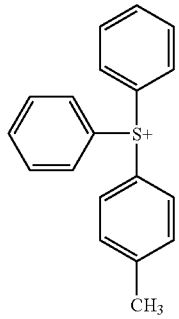

2-iii

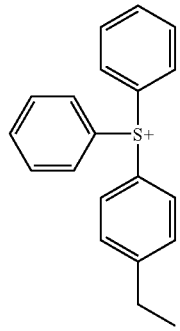

2-iv

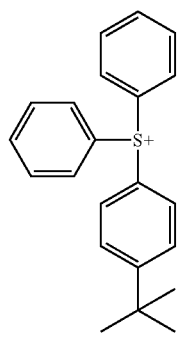

2-v

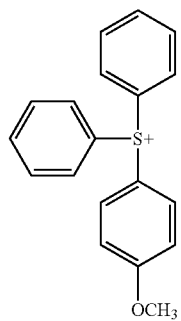

2-vi

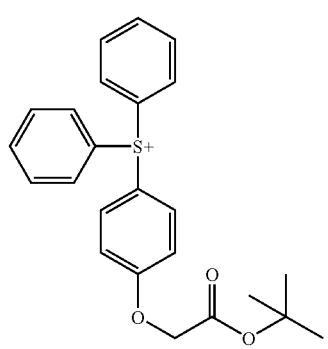

2-vii
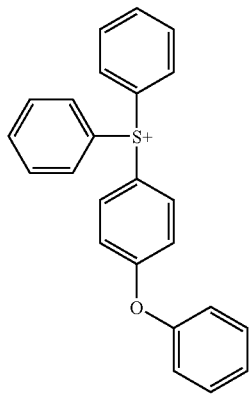
2-viii
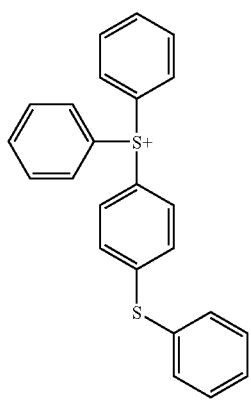
2-ix
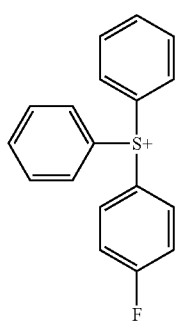
2-x
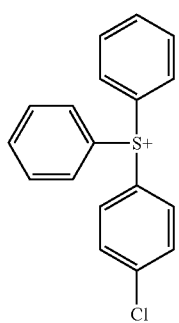
2-xi
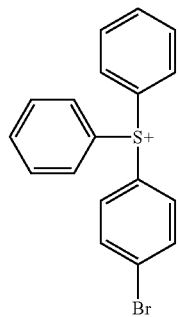
2-xii
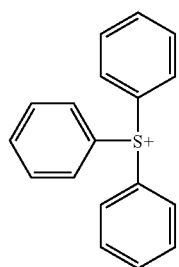
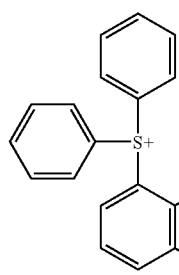
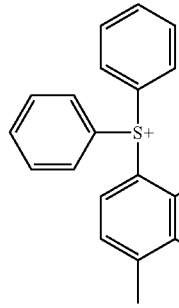
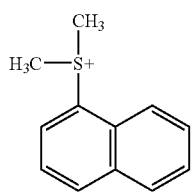
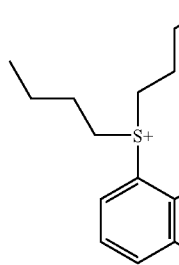

-continued

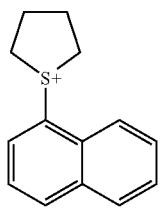

2-xvii

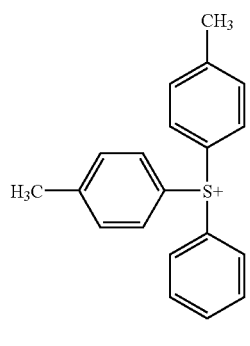

2-xviii

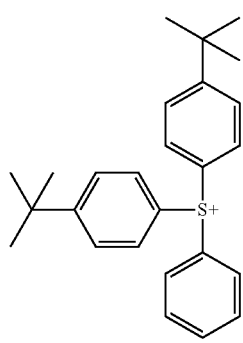

2-xix

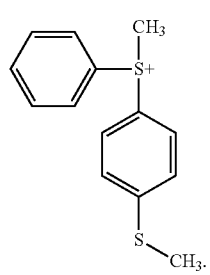

2-xx

-continued

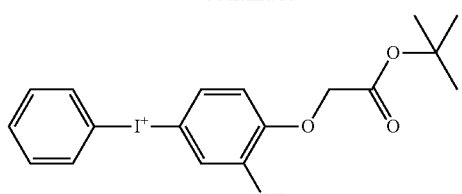

3-iii

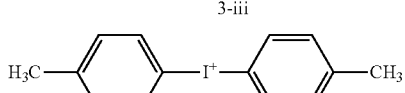

3-iv

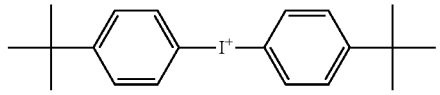

3-v

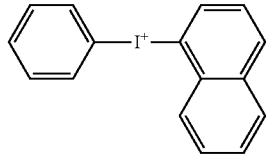

3-vi

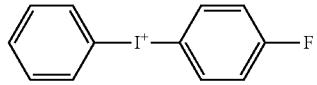

3-vii

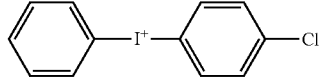

3-viii

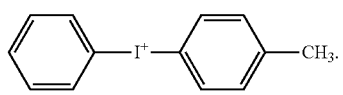

3-ix

7. The acid generating agent according to claim 5, wherein the compound of the formula (3a) or (3b) is selected from the group consisting of the compounds of the following formulas (3-i) to (3-ix):

[Formulas 3-i to 3-ix]

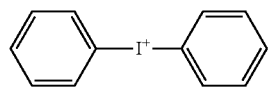

3-i

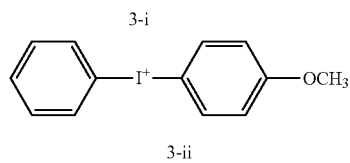

3-ii

8. The acid generating agent according to claim 1, wherein the acid generating agent is a salt represented by the following formula (4a), (4b), (4c) or (4d):

[Formula 4a]

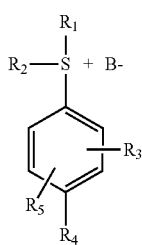

-continued

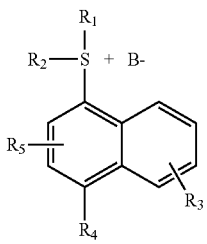
[Formula 4b]

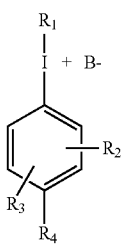
[Formula 4c]

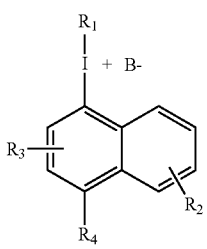
[Formula 4d]

wherein in the formulas (4a) and (4b), $R_1$ and $R_2$ each independently represent an alkyl group, an allyl group, a perfluoroalkyl group, a benzyl group or an aryl group; and $R_3$, $R_4$ and $R_5$ each independently represent a hydrogen atom, an alkyl group, a halogen atom, an alkoxy group, an aryl group, a thiophenoxy group, a thioalkoxy group or an alkoxycarbonylmethoxy group; in the formulas (4c) and (4d), $R_1$ represents an alkyl group, an allyl group, a perfluoroalkyl group, a benzyl group or an aryl group; and $R_2$, $R_3$ and $R_4$ each independently represent a hydrogen atom, an alkyl group, a halogen atom, an alkoxy group, an aryl group, a thiophenoxy group, a thioalkoxy group or an alkoxycarbonylmethoxy group; and in the above four formulas, B represents the anion moiety in the formula (1).

9. The acid generating agent according to claim 1, wherein the acid generating agent of formula (1) is produced by reacting a salt represented by the following formula (8) with a compound represented by the following formula (12):

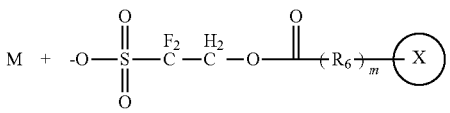
[Formula 8]

$A^+Z^-$ [Formula 12]

wherein X represents a monocyclic or polycyclic hydrocarbon group having 3 to 30 carbon atoms, and having at least one hydrogen atom substituted by an alkyl or alkoxy group which has 1 to 10 carbon atoms and may be unsubstituted or substituted with an ether group, an ester group, a carbonyl group, an acetal group, an epoxy group, a nitrile group or an aldehyde group, or by a perfluoroalkyl group having 1 to 4 carbon atoms, a hydroxyalkyl group having 1 to 10 carbon atoms or a cyano group; $R_6$ represents an alkyl group having 1 to 10 carbon atoms, an alkoxy group having 1 to 10 carbon atoms, or a heteroatom selected from the group consisting of N and S; m is an integer from 1 to 2; M is lithium (Li), sodium (Na) or potassium (K); Z is $OSO_2CF_3$, $OSO_2C_4F_9$, $OSO_2C_8F_{17}$, $N(CF_3)_2$, $N(C_2F_5)_2$, $N(C_4F_9)_2$, $C(CF_3)_3$, $C(C_2F_5)_3$, $C(C_4F_9)_3$, fluorine (F), chlorine (Cl), bromine (Br), iodine (I), $BF_4$, $ASF_6$ or $PF_6$; and A+ is an organic counterion.

10. The acid generating agent according to claim 9, wherein the salt represented by the formula (8) is produced by reacting an alcohol compound represented by the following formula (10) with a compound represented by the following formula (11):

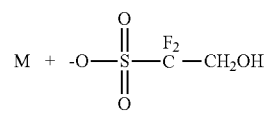
[Formula 10]

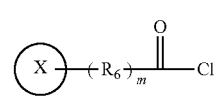
[Formula 11]

wherein in the formula (10), M is Li, Na or K; while in the formula (11), ring X represents a monocyclic or polycyclic hydrocarbon group having 3 to 30 carbon atoms, and having at least one hydrogen atom substituted by an alkyl or alkoxy group which has 1 to 10 carbon atoms and may be unsubstituted or substituted with an ether group, an ester group, a carbonyl group, an acetal group, an epoxy group, a nitrile group or an aldehyde group, or by a perfluoroalkyl group having 1 to 4 carbon atoms, a hydroxyalkyl group having 1 to 10 carbon atoms or a cyano group; $R_6$ represents an alkyl group having 1 to 10 carbon atoms, an alkoxy group having 1 to 10 carbon atoms, or a heteroatom selected from the group consisting of N and S; and m is an integer from 1 to 2.

11. The acid generating agent according to claim 10, wherein the alcohol compound represented by the formula (10) is produced by dissolving an ester compound represented by the following formula (9) in an alcoholic solvent, and then adding a reducing agent dropwise to the solution:

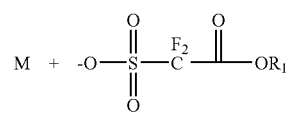
[Formula 9]

wherein $R_1$ is selected from the group consisting of hydrogen, methyl, trifluoromethyl, trichloromethyl, tribromomethyl and triiodomethyl; and M is Li, Na or K.

12. The acid generating agent according to claim 11, wherein the reducing agent is selected from sodium borohydride, lithium aluminum hydride ($LiAlH_4$), $BH_3$-THF, $NaBH_4$-$AlCl_3$, $NaBH_4$—LiCl, and $LiAl(OMe)_3$.

13. A chemically amplified resist composition comprising the acid generating agent according to claim 1.

* * * * *